US012350011B2

(12) United States Patent
Hoveling et al.

(10) Patent No.: US 12,350,011 B2
(45) Date of Patent: Jul. 8, 2025

(54) METHOD OF MEASURING A FLUORESCENCE SIGNAL, DETERMINING A PEAK FREQUENCY MAP AND PROVIDING A RISK PREDICTION VALUE, IMAGE CAPTURING AND PROCESSING DEVICE

(71) Applicant: Quest Photonic Devices B.V., Wieringerwerf (NL)

(72) Inventors: Richelle Johanna Maria Hoveling, Hoorn (NL); Richard Johannes Cornelis Meester, Wieringerwerf (NL)

(73) Assignee: Quest Photonic Devices B.V., Wieringerwerf (NL)

( * ) Notice: Subject to any disclaimer, the term of this patent is extended or adjusted under 35 U.S.C. 154(b) by 72 days.

(21) Appl. No.: 18/510,149

(22) Filed: Nov. 15, 2023

(65) Prior Publication Data

US 2024/0156350 A1     May 16, 2024

Related U.S. Application Data

(60) Provisional application No. 63/425,402, filed on Nov. 15, 2022.

(30) Foreign Application Priority Data

Oct. 23, 2023    (EP) .................................... 23205172

(51) Int. Cl.
    *A61B 5/00*       (2006.01)
    *G06T 11/60*      (2006.01)
    (Continued)

(52) U.S. Cl.
    CPC .......... *A61B 5/0071* (2013.01); *A61B 5/0077* (2013.01); *A61B 5/418* (2013.01);
    (Continued)

(58) Field of Classification Search
    CPC ..... A61B 5/0071; A61B 5/0077; A61B 5/418; A61B 5/4878; A61B 5/7267;
    (Continued)

(56) References Cited

U.S. PATENT DOCUMENTS

| | | | |
|---|---|---|---|
| 2002/0089561 A1* | 7/2002 | Weitzel | ................... G01F 17/00 |
| | | | 347/19 |
| 2003/0081138 A1* | 5/2003 | Hofer | ..................... H04N 23/70 |
| | | | 348/E5.034 |

(Continued)

FOREIGN PATENT DOCUMENTS

WO       2021/035094 A1    2/2021

OTHER PUBLICATIONS

Pin Van Den Hoven, MD., et al., "Normalization of Time-Intensity Curves for Quantification of Foot Perfusion Using Near-Infrared Fluorescence Imaging With Indocyanine Green", Journal of Endovascular Therapy, 2023, vol. 30(3) 364-371.

*Primary Examiner* — Bo Joseph Peng
(74) *Attorney, Agent, or Firm* — Scully, Scott, Murphy & Presser, P.C.

(57) ABSTRACT

An image capturing and processing device to measure a fluorescence signal in tissue and image a surface of a body part. The device includes a fluorescence image sensor to capture a fluorescence image. The fluorescence image sensor captures time sequence of fluorescence images A peak frequency map unit determines a peak frequency map for an area of interest in the fluorescence images by analyzing the time sequence of fluorescence images. The analyzing includes: determining a time-dependent intensity curve, identifying peaks in the time-dependent intensity curve and determining one or more of a frequency of the identified peaks and a maximum high of the identified peaks, generating a graphic representation of one or more of the determined frequency and maximum high and including the same (Continued)

in the peak frequency map. The peak frequency map together with one or more of the visible light image and the fluorescence image are outputted.

38 Claims, 12 Drawing Sheets

(51) Int. Cl.
*G16H 30/40* (2018.01)
*G16H 50/30* (2018.01)

(52) U.S. Cl.
CPC .......... *A61B 5/4878* (2013.01); *A61B 5/7267* (2013.01); *A61B 5/7275* (2013.01); *A61B 5/7425* (2013.01); *G06T 11/60* (2013.01); *G16H 30/40* (2018.01); *G16H 50/30* (2018.01); *G06T 2210/41* (2013.01)

(58) Field of Classification Search
CPC . A61B 5/7275; A61B 5/7425; A61B 1/00006; A61B 1/000094; A61B 1/000096; A61B 1/00167; A61B 1/00186; A61B 1/042; A61B 1/043; A61B 1/0638; A61B 1/07; A61B 1/3132; A61B 5/0035; A61B 5/0084; A61B 5/742; G06T 11/60; G06T 2210/41; G06T 7/0012; G16H 30/40; G16H 50/30; G16H 10/60; G16H 20/30; G16H 20/40; G16H 30/20; G16H 40/67; G16H 50/20; G16H 50/70

See application file for complete search history.

(56) References Cited

U.S. PATENT DOCUMENTS

| | | | |
|---|---|---|---|
| 2003/0090587 A1* | 5/2003 | Hofer | H04N 23/673 348/370 |
| 2010/0003695 A1* | 1/2010 | Geddes | G01N 21/76 250/361 C |
| 2017/0002330 A1* | 1/2017 | Vunjak-Novakovic | C12N 5/0657 |
| 2019/0355116 A1 | 11/2019 | Gurevich | |
| 2020/0323430 A1 | 10/2020 | Tsumatori | |
| 2022/0322922 A1 | 10/2022 | Meester | |

* cited by examiner

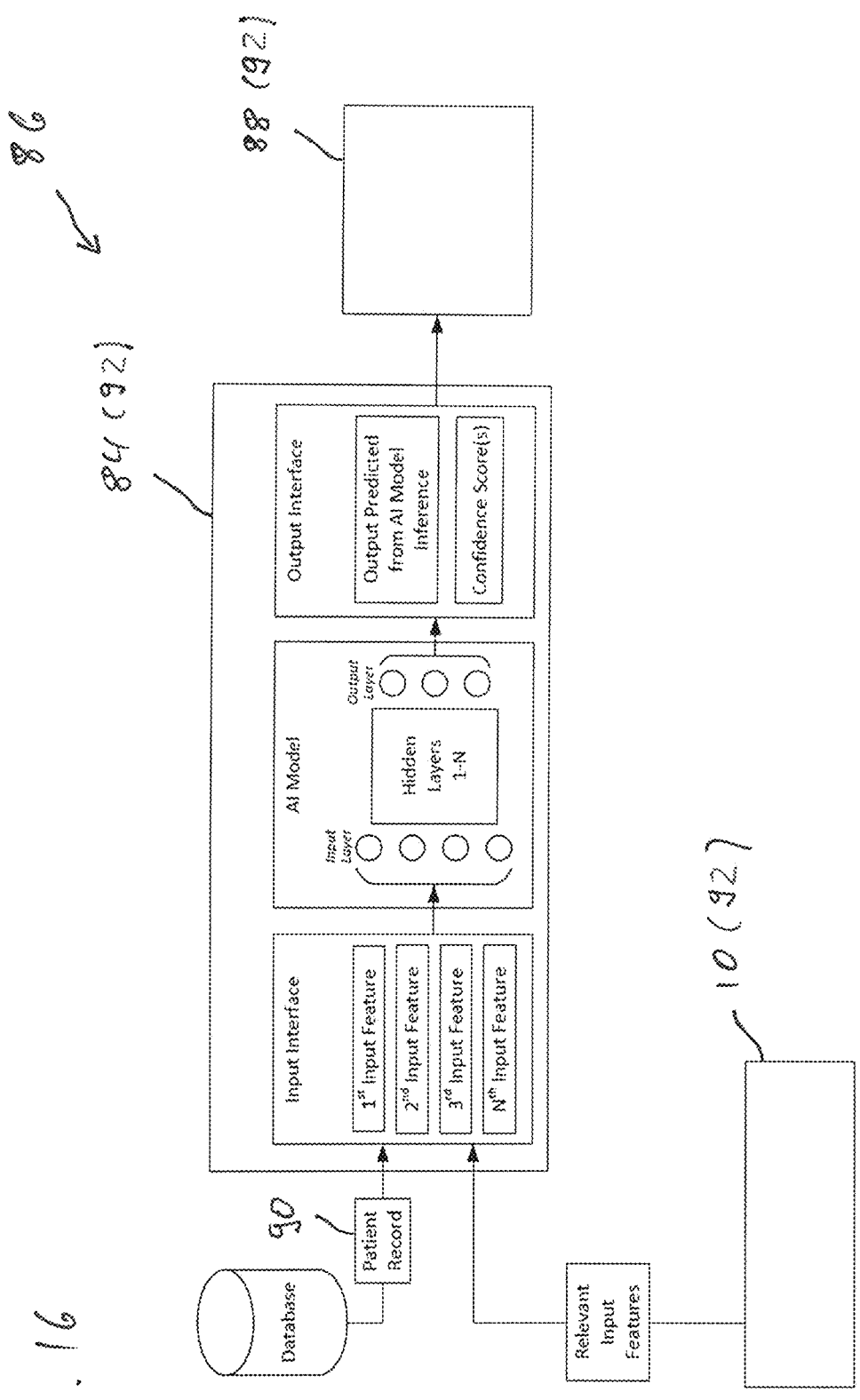

METHOD OF MEASURING A FLUORESCENCE SIGNAL, DETERMINING A PEAK FREQUENCY MAP AND PROVIDING A RISK PREDICTION VALUE, IMAGE CAPTURING AND PROCESSING DEVICE

CROSS-REFERENCE TO RELATED APPLICATION

The present application is based upon and claims the benefit of priority from U.S. Provisional Application No. 63/425,402 filed on Nov. 15, 2022, and EP 23205172 filed on Oct. 23, 2023, the entire contents of each of which is incorporated herein by reference.

BACKGROUND

Field

The present disclosure relates to a method of measuring a fluorescence signal in a tissue of a body part, to which a fluorescent agent has been added, and of imaging a surface of the body part, wherein the tissue to which the fluorescent agent has been added forms part of the body part. The present disclosure further relates to an image capturing and processing device configured to measure a fluorescence signal in a tissue of a body part to which a fluorescent agent has been added and to image a surface of the body part, wherein the tissue to which the fluorescent agent has been added forms part of the body part. Furthermore, the present disclosure relates to an endoscope or laparoscope comprising the image capturing and processing device.

The present disclosure also relates to a method of diagnosing lymphatic dysfunction, such as lymphedema, and to a method of long-term therapy of lymphatic dysfunction, such as lymphedema.

The method and the image capturing and processing device relate to imaging and measuring of the lymphatic dysfunction, such as lymphatic function, and further relates to one or more of the diagnosis, treatment and prevention of lymphatic dysfunction, such as lymphedema.

The present disclosure also relates to a method of providing a risk prediction value based on measuring of a fluorescence signal in a tissue of a body part, to which a fluorescent agent has been added. Furthermore, the present disclosure relates to a computer-based clinical decision support system (CDSS) for providing of a risk prediction value based on a measurement of a fluorescence signal in a tissue of a body part, to which a fluorescent agent has been added.

Prior Art

Lymphedema is a lymphatic dysfunction and results in an accumulation of lymphatic fluid in the body's tissue. While oxygenated blood is pumped via the arteries from the heart to the tissue, deoxygenated blood returns to the heart via the veins. Because the pressure level on the arterial side is much higher than on the vein side, a colorless fluid part of the blood is pushed into the space between the cells. Typically, more fluid is pushed out, than reabsorbed on the vein side. The excess fluid is transported by the lymphatic capillaries. Furthermore, the fluid carries away local and foreign substances such as larger proteins and cellular debris. Once in the lymphatic system, this fluid including the transported substances is referred to as lymph or lymph fluid.

The lymphatic system comprises lymphatic vessels having one way valves similar to vein valves for transporting the lymph to the next lymph node. The lymph node performs removal of certain substances and cleans the fluid before it drains back to the blood stream.

If the lymphatic system becomes obstructed in that the lymph flow is blocked or not performed at the desired level, the lymph fluid accumulates in the interstitial space between the tissue cells. This accumulation, which is due to an impairment of lymphatic transport, is called lymphedema. The accumulation of lymph can cause inflammatory reaction which damages the cells surrounding the affected areas. It can further cause fibrosis which can turn into a hardening of the affected tissue.

Because lymphedema is a lifelong condition for that no cure or medication exists, early diagnoses and appropriate early counter measures for improving drainage and reducing the fluid load are of high importance for patients' well-being and recovering. Possible treatments such as lymphatic massage and compression bandages up to surgery depend on the level of severity, which is a four stage system defined by the World Health Organization (WHO) as follows:

Stage 1: a normal flow in the lymphatic system. No signs or symptoms.
Stage 2: accumulation of fluid with swelling.
Stage 3: permanent swelling that does not resolve with elevation of the affected limb or body part.
Stage 4: elephantiasis (large deformed limb), skin thickening with "wart like" growth and extensive scarring.

For diagnosis of the function of the lymphatic system, commonly used techniques are a manual inspection of the affected limb or body part by a physician. A known imaging technique is lymphoscintigraphy. In this technique, a radio tracer is injected in the tissue of the affected body part and subsequently MRI (Magnetic Resonance Imaging), CT (Computer Tomography), a PET-CT-scan (Positron Emission Tomography) or ultrasound imaging is performed.

A relatively new imaging technique is infrared fluorescence imaging using a fluorescent dye, for example ICG (Indocyanine Green). ICG is a green colored medical dye that is used for over 40 years. The dye emits fluorescent light when exited with near infrared light having a wavelength between 600 nm and 800 nm. Due to this excitation, ICG emits fluorescence light between 750 nm and 950 nm. The fluorescence of the ICG dye can be detected using a CCD or CMOS sensor or camera. The fluorescent dye is administered to the tissue of an affected limb or body part and the concentration and flow of the lymphatic fluid can be traced on the basis of the detected fluorescence light.

Lymphatic dysfunction is caused by insufficient circulation of lymphatic fluid in the body's tissue. Tissue perfusion in general is an important biomarker in many clinical findings. For example, it is an indicator for successful recovery after a surgery, for example in gastrointestinal surgery.

Fluorescence imaging provides valuable information for the assessment of tissue perfusion. Data analysis is typically performed by analyzing the time-intensity curves of the fluorescence intensity. The time-intensity curves can be extracted from time dependent recordings of fluorescence images. The time-intensity data is for example extracted per pixel or can be averaged across a certain region. The time-intensity curves can be analyzed by fitting of a model, wherein the coefficients of the model do give certain information on physiological parameters. However, the coefficients of the model more or less accurately describe the shape of the time-intensity curve and are not directly linked to the underlying biological processes. Interpretation of the derived coefficients can therefore be sometimes difficult.

SUMMARY

It is an object to provide an enhanced method of measuring a fluorescence signal and an enhanced image capturing and processing device as well as an enhanced endoscope or laparoscope, wherein an enhanced fluorescence imaging output can be provided. Furthermore, an object is to provide an enhanced method of diagnosing lymphedema and an enhanced method of long-term therapy of lymphedema.

It is an object to provide an enhanced method of providing a risk prediction value based on a fluorescence signal and an enhanced computer-based clinical decision support system (CDSS) for providing of a risk prediction value.

Accordingly, a method of measuring a fluorescence signal in a tissue of a body part, to which a fluorescent agent has been added, and of imaging a surface of the body part, wherein the tissue to which the fluorescent agent has been added forms part of the body part is provided. The method comprising:
- capturing at least one fluorescence image in an area of examination by illuminating the tissue with excitation light having a wavelength suitable to generate emitted light by excited emission of the fluorescent agent, and by spatially resolved measurement of the emitted light so as to provide the fluorescence image,
- capturing at least one visible light image of a surface of the body part in the area of examination, wherein one or more of a viewing direction and a perspective of the fluorescence image and the visible light image are linked via a known relationship,
- repeating the capturing the fluorescence image to capture a plurality of fluorescence images over time so as to provide a time sequence of fluorescence images, and the repeating of capturing the visible light image to capture a plurality of visible light images over time can provide a time sequence of visible light images,
- determining a peak frequency map for an area of interest in the fluorescence images by analyzing the time sequence of fluorescence images by performing:
    - determining a time-dependent intensity curve of at least one pixel in the area of interest,
    - identifying peaks in the time-dependent intensity curve and
    - determining one or more of a frequency of the identified peaks and a maximum high of the identified peaks, and
    - generating a graphic representation of one or more of the determined frequency and maximum high for the at least one pixel and including the same in the peak frequency map, and
- outputting the peak frequency map together with one or more of the visible light image and the fluorescence image.

An important information for diagnosing lymphedema is the speed of the lymphatic transport up the lymphatic system. While a rapid transport of the lymphatic fluid indicates that the lymphatic veins are intact and there is no lymphedema, a slow transport of the lymphatic fluid is a strong indication that the patient developed lymphedema in a stage that should undergo therapeutic treatment. The transport of the lymphatic fluid is visible in the fluorescence image because a fluorescent agent, for example ICG (indocyanine green), has been administered to a tissue of a body part which is subjected to show insufficient lymphatic function. By watching the fluorescent image overtime, the take up of the lymphatic fluid in the lymphatic system can be observed. In a healthy lymphatic system, the fluorescent agent is quickly taken up by the lymphatic system together with the lymphatic fluid. The lymphatic veins rapidly transport the lymphatic fluid in linear channels. These lymphatic vessels include one way valves to prevent backflow of the fluid.

In a healthy lymphatic system, there is rhythmic transport of the lymphatic fluid in the lymphatic vessels. This process can be observed in time-resolved fluorescent images. The rhythmic transport of the lymphatic fluid leads to an intensity oscillation in certain areas of the fluorescence image. These areas correspond to the locations of the lymphatic vessels.

In case of lymphedema, the obstruction of lymphatic fluid flow leads to an increase in pressure within the lymphatic channels and due to this, lymphatic fluid leaks out into subcutaneous tissue. For prevention of lymphedema, an early diagnosis and treatment of the disease is of utmost importance. In the lymphatic system of a patient who developed lymphedema, significantly reduced transport of the lymphatic fluid can be observed. Again, this phenomenon can be detected by analyzing the time-resolved series of fluorescence images. Hence, the analysis of the plurality of fluorescence images that have been taken over time, can be a key issue for reliable and early diagnosis of lymphedema.

After administration of the fluorescent agent, which occurs before the method of measuring the fluorescent signal starts, a fluorescence signal can be tracked and analyzed on the basis of the captured series of fluorescence images. The captured images are time-resolved fluorescence images representing a time sequence of fluorescence images.

The fluorescent agent is for example ICG (Indocyanine Green) or methylene blue. Within the context of this specification, the term "fluorescent dye" or "dye" (also referred to as "fluorochrome" or "fluorophore") refers to a component of a molecule, which causes the molecule to be fluorescent. The component is a functional group in the molecule that absorbs energy of a specific wavelength and re-emits energy at a different specific wavelength. In various aspects, the fluorescent agent comprises a fluorescence dye, an analogue thereof, a derivative thereof, or a combination of these. Appropriate fluorescent dyes include, but are not limited to, indocyanine green (ICG), fluorescein, methylene blue, isosulfan blue, Patent Blue, cyanine5 (Cy5), cyanine5.5 (Cy5.5), cyanine7 (Cy7), cyanine7.5 (Cy7.5), cypate, silicon rhodamine, 5-ALA, IRDye 700, IRDye 800CW, IRDye 800RS, IRDye 800BK, porphyrin derivatives, Illuminare-1, ALM-488, GCP-002, GCP-003, LUM-015, EMI-137, SGM-101, ASP-1929, AVB-620, OTL-38, VGT-309, BLZ-100, ONM-100, BEVA800.

The analysis of the lymphatic flow, does however not stop at the mere observation of the time resolved series of fluorescence images. The time series of fluorescence images is analyzed by defining an area of interest in the fluorescence images. This area of interest ranges from a single pixel in the fluorescence image up to the full scale fluorescence image, i.e. the complete fluorescence image. In many cases, the area of interest will be somewhat in between. For example, a selection rectangle can be defined on a screen using a suitable tool that can be operated by an input hardware, for example with a mouse or trackball. In this area of interest, the fluorescence images are analyzed over time. This can be the entire time of examination during which the time sequence of fluorescence images was captured or a predetermined or selected time span.

For simplification of the explanations, reference will be made to the analysis of a single pixel in the fluorescence image. In other words, the area of interest is, for the sake of simplification only, a single pixel. A similar approach applies when a plurality of pixels are analyzed.

The intensity of the pixel under inspection in the time series of fluorescence images can be analyzed and a time dependent intensity curve for said pixel can be determined. The time dependent intensity curve typically shows various peaks, if the pixel that is analyzed is located in an area of the fluorescence image, in which transport of the lymphatic fluid takes place. This transport can be indicated by a varying intensity of the fluorescence signal. For example, the intensity of the fluorescence signal will follow the oscillation of the lymphatic fluid in a lymphatic channel.

After determination of the time dependent intensity curve, the curve can be analyzed and peaks in the intensity are identified. A maximum height of the peak and a location of the peak can be determined. For example, this can be performed by slope analysis or with any other suitable approach. Based on the information on the locations of the peaks, a frequency of the identified peaks can be calculated. A unit of this frequency is for example peaks per second or peaks per frame or peaks per 100 frames, etc. The information on the frequency of peaks can be output together with the visible image of the surface of the patient's body part. Based on this information, the operator can be provided with information on a lymphatic transport in the area of interest. A high frequency can be indicative of the typical pulsing transport of lymphatic fluid and thereby can clearly indicate a high transport volume. The value of the frequency can be output as a digit, in a color scale or in any other suitable information.

As a further or alternative information, the maximum height of the peaks can be analyzed. The higher the peaks of the fluorescence signal are, the higher the concentration of lymphatic fluid at the analyzed pixel in the area of interest (or in the area of interest when considered in its entirety). A maximum height of the identified peaks can be determined. This information can also be very valuable, for example, in combination with the information about the frequency of peaks. While the maximum value gives an information on the concentration of lymphatic fluid, the frequency gives an information on the transport of the lymphatic fluid.

If the above described approach is executed for all pixels in the area of interest, a map of the frequencies of maxima, a so called frequency map can be generated. The map can be displayed in a color scale. Similarly, a map of the maximum values of the detected peaks can be generated. This map can also be displayed in a color scale. The maps can be shown side by side with the fluorescence image and also in combination with the visible light image. The combination with the visible light image can enable the user to pinpoint a position on the patient's body part, at which certain diagnostic findings have been made. This can enable for example a physician to provide the patient with a tailored therapy of the detected lymphedema.

Additional information about for example a status of the frequency or a rate can be included in the output of the peak frequency map. It can be represented in the form of a scoring probability indicated in good or bad color indication etc. The detection of the maxima in the time dependent intensity curve can be performed by for example a slope analysis of the intensity curve. The detection of the peaks can also be based on threshold analysis, which means that every part of the curve that is above a certain threshold value can be considered a peak. The output of the peak frequency map can be a color indication, a graph, a value or a false color indicating the amount of the value or even a simple table. An easy to understand graphic representation is the intensity plot.

According to an embodiment, the generating of a graphic representation can include generating an intensity plot, which can be indicative of one or more of the determined frequency and the maximum high of the identified peak at a position of the least one pixel in the area of interest.

The intensity plot can be a false color representation of one or more of the frequency of the identified peaks and of a maximum height of the identified peaks. It can also be a plot showing contour lines, such as contour lines having the colors taken from the intensity plot in false color representation.

To further simplify the interpretation of the measurement results, a superposition of the peak frequency map and one or more of the fluorescence image and the visible light image can be performed.

According to an embodiment, the method can further comprise:
  superimposing the peak frequency map and the fluorescence image so as to provide a peak/fluorescence overlay image,
  one or more of outputting the peak/fluorescence overlay image as the output of the peak frequency map together with the fluorescence image, and
  superimposing the peak frequency map and the visible light image so as to provide a peak/visible overlay image, and
  outputting the peak/visible overlay image as the output of the peak frequency map together with the visible light image.

The superposition of the peak frequency map with the fluorescence image can simplify the interpretation of the fluorescence image. The superposition of the peak frequency map with a visible light image can enable the user to pinpoint certain areas, in which for example particular treatment of lymphedema is advisable.

Furthermore, the capturing of the fluorescence image and the capturing of the visible light image can be performed simultaneously, such as in absence of time-switching between a signal of the fluorescence image and a signal of the visible light image.

The fluorescence image and the visible light image can be captured simultaneously. As a result, a perfect match can be achieved between the measurement of the fluorescence signal, which means the fluorescence image, and the visible light image showing the surface of the body part under inspection. Based on this information, tailored and spatial accurate precise treatment of for example a lymphatic dysfunction can be performed. The same can be applied to the possibility for a diagnosis.

According to still another embodiment, the method can further comprise:
  repeating the capturing of the fluorescence image and capturing the visible light image to provide a series of fluorescence images and a series of visible light images, wherein the images of the series show different overlapping areas of examination of the body part,
  applying a stitching algorithm on the series of visible light images to generate a large visible light image, wherein the stitching algorithm determines and applies a set of stitching parameters, applying the stitching algorithm on the series of fluorescence images to generate a large fluorescence image, wherein the stitching algorithm applies the set of stitching parameters determined when performing the stitching of the visible light images, wherein the outputting includes outputting the large visible light image together with the large fluorescence image and the peak frequency map.

By application of the stitching algorithm, a larger area of the body part can be inspected. The stitching algorithm can perform the reconstruction and stitching of the series of fluorescence images based on the set of stitching parameters, which have been previously determined when performing the stitching of the visible light images. During the stitching, only one image of the time sequence of fluorescence images and of the time series of visible light images can be used. The application of the previously determined stitching parameters is possible because fluorescence images typically offer rare special features that are suitable for performance of the stitching process. Because the visible light image and the fluorescence image are linked by the known and constant relationship with respect to one or more of the viewing direction and perspective, the parameters of the stitching algorithm used for the visible light images can also be applied for a stitching of the fluorescence images. This can significantly enhance the stitching process and the achievable results.

According to another embodiment, the measurement of the fluorescence signal can be performed on a tissue, to which at least a first and a second fluorescent agent has been added, wherein the capturing of the fluorescence image can comprise:
  capturing a first fluorescence image in a first wavelength range, which is generated by illuminating the tissue with first excitation light having a first wavelength suitable to generate emitted light by a first excited emission of the first fluorescent agent, and
  capturing a second fluorescence image in a second wavelength range, which is generated by illuminating the tissue with second excitation light having a second wavelength suitable to generate emitted light by a second excited emission of the second fluorescent agent,
  wherein the capturing of a time sequence of fluorescence images, the determining of a peak frequency map and the outputting of the peak frequency map together with the visible light image can be performed for the first and the second fluorescence image.

Fluorescence imaging based on two fluorescent agents can be desirable since different fluorescent dyes open the field for differential diagnosis. The first fluorescent agent can be for example ICG and the second fluorescent agent can be methylene blue. The first fluorescence image can be captured in the wavelength range which is between 700 nm and 800 nm, if methylene blue is used as the first fluorescent agent or dye. The second fluorescence image can be captured in the wavelength range, which is between 800 nm and 900 nm, if ICG is used as the second fluorescent agent or dye. The method can be performed with different fluorescent agents and dyes. Basically, any combination of an appropriate dye plus the suitable or matching excitation light source can be applied.

Often, the function of the lymphatic system is affected in a limb of the body. However, the method of measuring the fluorescence signal is not limited to the inspection of a limb. The method generally refers to the inspection of a body part, which can be a limb of a patient but also the corpus, the head, the neck, the back or any other part of the body. It is also possible that the body part is an organ, such as an inner organ. The method of measuring the fluorescence signal can be used an indicator for the lymphatic flow and it can also be performed during open surgery. The same applies to a situation in which the surgery is minimally invasive surgery, performed using an endoscope or laparoscope.

Within the context of this specification, a "visible light image" is an image of the real world situation. It reproduces an image impression similar to what can be seen by the human eye. Unlike the human eye, the visible light image can be a color image, a grey scale image or even false color scale plot. The visible light image shows a surface of the body part comprising the tissue to which the fluorescent agent has been administered. If the tissue is arranged at the surface of the body part, for example when an inner organ is inspected, the imaging of the surface of the body part includes imaging of the surface of the tissue.

Furthermore, the capturing of the first fluorescence image and the capturing of the second fluorescence image can be performed simultaneously, such as in absence of time-switching between a signal of the first fluorescence image and a signal of the second fluorescence image.

Simultaneous capture of the first and second fluorescence image can result in a measurement, in which the information derived from the first fluorescence image and the information derivable from the second fluorescence image can refer to a same point in time. Features or information that can be obtained from a comparison of the two images are therefore not deteriorated by a time dependent change in the body part, for example a quick fluctuation of lymphatic fluid. This can enhance the quality of the measurement.

According to another embodiment, the viewing direction and the perspective of the fluorescent image and the visible light image can be identical and, the fluorescence image and the visible light image can be captured through one of the same objective lens. Capturing of both images through one single objective lens can provide an almost perfect alignment of the viewing direction and the image perspective.

The fluorescence image and the visible light image can be captured in the absence of time switching. This can be performed by an image capturing device, which comprises a prism assembly and a plurality of image sensors. Fluorescent light and visible light enter the prism assembly as a common light bundle and through the same entrance surface of the prism assembly. The prism assembly or structure can also comprise filters for separating the visible wavelength range from the infrared wavelength range at which the exited emission of the fluorescent agent typically takes place. The different wavelength ranges can be directed to different sensors. These sensors can be independently operated, wherein no time switching of the signals of the sensors is necessary. Thus, the infrared picture, which is the fluorescence picture, and the visible light picture can be captured exactly at the same time using separate image sensors. Hence, the images can be captured with the high frame repeat rate of for example 60 frames per second or even higher. Higher framerates can typically not be achieved when performing time switching. Furthermore, when the fluorescence image and the visible light image are captured on individual sensors, these sensors can both be arranged exactly in focus. Furthermore, the settings of the sensors can be individually adjusted, taking into account the requirements for image capture of the visible light image and the fluorescence image. This relates for example to an adjustment of the sensor gain, the noise reduction or an exposure time.

An image capturing and processing device is also provided. Such device is configured to measure a fluorescence signal in a tissue of a body part, to which a fluorescent agent has been added, and to image a surface of the body part, wherein the tissue to which the fluorescent agent has been added forms part of the body part, the image capturing and processing device comprising:
  an image capturing device, which comprises:
    an illumination unit configured to illuminate the tissue with excitation light having a wavelength suitable to generate emitted light by excited emission of the fluorescent agent,
    a fluorescence imaging unit configured to capture a fluorescence image in an area of examination by illuminating the tissue with excitation light having a wavelength suitable to generate emitted light by excited emission of the fluorescent agent, and by spatially resolved measurement of the emitted light so as to provide the fluorescence image,
    a visible light imaging unit configured to capture a visible light image of a surface of the body part in the area of examination, wherein one or more of a viewing direction and a perspective of the fluorescence image and the visible light image are linked via a known relationship,
    wherein the fluorescence imaging unit is further configured to capture a plurality of fluorescence images over time so as to provide a time sequence of fluorescence images, and
    wherein the visible light imaging unit can be configured to capture a plurality of visible light images over time so as to provide a time sequence of visible light images,
  the image capturing and processing device further comprising a processing device, which comprises:
    a peak frequency map unit configured to determine a peak frequency map for an area of interest in the fluorescence images by analyzing the time sequence of fluorescence images, wherein the peak frequency map unit is configured to:
      determine a time-dependent intensity curve of at least one pixel in the area of interest,
      identify peaks in the time-dependent intensity curve,
      determine one or more of a frequency of the identified peaks and a maximum high of the identified peaks, and
      generate a graphic representation of one or more of the determined frequency and maximum high for the at least one pixel and including the same in the peak frequency map, and
    an output unit configured to output the peak frequency map together with one or more of the visible light image and the fluorescence image.

Same or similar advantages, which have been mentioned with respect to the method of measuring the fluorescence signal apply to the image capturing and processing device in the same or similar way and shall therefore not be repeated.

According to an embodiment, the peak frequency map unit can be further configured in that the generation of the graphic representation can include generating an intensity plot, which is indicative of one or more of the determined frequency and the maximum high of the identified peak at a position of the at least one pixel in the area of interest.

Furthermore, the processing device can comprise:
  the superimposing unit can be configured to superimpose the peak frequency map and the fluorescence image so as to provide a peak/fluorescence overlay image,
  one or more of the output unit can be further configured to output the peak/fluorescence overlay image as the output of the peak frequency map together with the fluorescence image, and
  the superimposing unit can be configured to superimpose the peak frequency map and the visible light image so as to provide a peak/visible overlay image, and
  the output unit can be further configured to output the peak/visible overlay image as the output of the peak frequency map together with the visible light image.

According to still another embodiment, the image capturing device, such as the fluorescence imaging unit and the visible light imaging unit, can be further configured to:
  repeat the capturing of the fluorescence image and the capturing of the visible light image to provide a series of fluorescence images and a series of visible light images, wherein the series show different overlapping areas of examination of the body part,
  wherein the processing device can further comprise:
    a stitching unit configured to apply a stitching algorithm on the series of visible light images and to generate a large visible light image, wherein the stitching algorithm determines and applies a set of stitching parameters, and
    the stitching unit is further configured to apply the stitching algorithm on the series of fluorescence images and to generate a large fluorescence image, wherein the stitching algorithm applies the set of stitching parameters determined when performing the stitching of the visible light images,
  wherein the output unit can be further configured to output the large visible light image together with the large fluorescence image and the peak frequency map.

Furthermore, according to an embodiment, the fluorescence imaging unit and the visible light imaging unit can be further configured to repeat the capturing of the fluorescence image and the capturing of the visible light image to provide a series of fluorescence images and a series of visible light images, wherein the images of the series show different overlapping areas of examination of the body part, the processing device can further comprise:
  a stitching unit configured to apply a stitching algorithm on the series of visible light images to generate a large visible light image, wherein the stitching algorithm determines and applies a set of stitching parameters,
  wherein the stitching unit can be further configured to apply the stitching algorithm on the series of fluorescence images to generate a large fluorescence image, wherein the stitching algorithm applies the set of stitching parameters determined when performing the stitching of the visible light images,
  wherein the output unit can be configured to output the large visible light image together with the large fluorescence image and the peak frequency map.

The fluorescence imaging unit and the visible light imaging unit can be configured in that the viewing direction and the perspective of the fluorescence image and the visible light image can be identical, wherein the fluorescence imaging unit and the visible light imaging unit wherein configured in that the fluorescence image and the visible light image are captured through a same objective lens.

According to still another embodiment, the fluorescence imaging unit and the visible light imaging unit can be configured to capture the fluorescence image and the visible light image simultaneously, such as in absence of time-switching between a signal of the fluorescence image and a signal of the visible light image.

According to still another embodiment, the image capturing device can further comprise:
- a dichroic prism assembly configured to receive fluorescent light forming the fluorescence image and visible light forming the visible light image through an entrance face, comprising: a first prism, a second prism, a first compensator prism located between the first prism and the second prism,
- a further dichroic prism assembly for splitting the visible light in three light components, and a second compensator prism located between the second prism and the further dichroic prism assembly,
- wherein the first prism and the second prism each have a cross section with at least five corners, each corner having an inside angle of at least 90 degrees, wherein the corners of the first prism and the second prism each have a respective entrance face and a respective exit face, and are each designed so that an incoming beam which enters the entrance face of the respective prism in a direction parallel to a normal of said entrance face is reflected twice inside the respective prism and exits the respective prism through its exit face parallel to a normal of said exit face,
- wherein the normal of the entrance face and the normal of the exit face of the respective prism are perpendicular to each other; and
- wherein, when light enters the first prism through the entrance face, the light is partially reflected towards the exit face of the first prism thereby traveling a first path length from the entrance face of the first prism to the exit face of the first prism, and the light partially enters the second prism via the first compensator prism and is partially reflected towards the exit face of the second prism, thereby traveling a second path length from the entrance face of the first prism to the exit face of the second prism,
- wherein the first prism is larger than the second prism so that the first and the second path lengths are the same.

The above-referred five prism assembly allows capturing two fluorescence images at two wavelengths and three colors for the visible light imaging all at the same time. The colors for the visible light image can be for example red, blue and green. The five prism assembly can allow the optical length of the light traveling from the entrance surface to a respective one of the sensors to have identical length. All sensors can be arranged in focus and furthermore, there is no timing gap between the signals of the sensors. The device does not require time switching of the received signals. The prism assembly can furthermore be compact and does not unnecessarily enlarge the capturing device.

According to still another embodiment, the image capturing device, can define a first, a second, and a third optical path for directing fluorescence light and visible light to a first, a second, and a third sensor, respectively, the image capturing device can further comprise a dichroic prism assembly, configured to receive the fluorescent light and the visible light through an entrance face, the dichroic prism assembly can comprise: a first prism, a second prism and a third prism, each prism having a respective first, second, and third exit face, wherein: the first exit face is provided with the first sensor, the second exit face is provided with the second sensor, and the third exit face is provided with the third sensor, wherein the first optical path can be provided with a first filter, the second optical path is provided with a second filter, and the third optical path is provided with a third filter, wherein the first, second, and third filters, in any order, can be a green filter, an infrared filter, and a red/blue patterned filter comprising red and blue filters in alternating pattern so that half of the light received by the red/blue patterned filter goes through a blue filter and half of the light received by the red/blue patterned filter goes through a red filter.

Furthermore, according to another embodiment, the first, second, and third filters, in any order, can be a red/green/blue patterned filter (RGB filter), a first infrared filter, and a second infrared filter, wherein the first and second infrared filter can have different transmission wavelengths.

In other words, the first and second infrared filters can be for filtering IR-light in different IR wavelength intervals, for example in a first IR-band in which typical fluorescent dyes emit a first fluorescence peak and in a second IR-band in which a typical fluorescent dye emits a second fluorescence peak. Typically, the second IR-band wherein located at higher wavelength compared to the first IR-band. The first and second infrared filters can also be adjusted to emission bands of different fluorescent agents. Hence, the emission of for example a first fluorescent agent passes the first filter (and can be blocked by the second filter) and can be detected on the corresponding first sensor and the emission of the second fluorescent agent passes the second filter (and can be blocked by the first filter) and can be detected on the corresponding second sensor. For example, the first filter can be configured to measure the fluorescence emission of methylene blue and the second filter can be configured to measure the fluorescence emission of ICG.

Also with respect to the embodiments of the image capturing and processing device, same or similar advantages apply, which have been mentioned with respect to the method of measuring the fluorescence signal.

An endoscope or laparoscope is also provided, which can be configured in that it serves as the image capturing device in the image capturing and processing device according to one or more of the previously mentioned embodiments. The device for image capturing and processing can be used in open surgery as well as during surgery using the endoscope or laparoscope. Same or similar advantages which have been mentioned with respect to one or more of the method and the device apply to the endoscope or laparoscope in the same or similar way.

Still further provided is a method of diagnosing lymphatic dysfunction, such as lymphedema, comprising:
- administering a fluorescent agent to a body part,
- measuring a fluorescence signal in a tissue of the body part, to which the fluorescent agent has been administered, and of imaging a surface of the body part, wherein the tissue to which the fluorescent agent has been added forms part of the body part,
- capturing a fluorescence image by illuminating the tissue with excitation light having a wavelength suitable to generate emitted light by excited emission of the fluorescent agent, and by spatially resolved measurement of the emitted light so as to provide the fluorescence image,
- capturing a visible light image of a surface of the body part in the area of examination, wherein one or more of a viewing direction and a perspective of the fluorescence image and the visible light image are linked via a known relationship,
- repeating the capturing of the fluorescence image to capture a plurality of fluorescence images over time so as to provide a time sequence of fluorescence images, and where the repeating of the capturing of the visible light
image to capture a plurality of visible light images can
be over time so as to provide a time sequence of visible
light images,
determining a peak frequency map for an area of interest
in the fluorescence images by analyzing the time
sequence of fluorescence images, the analysis comprising:
determining an time-dependent intensity curve of at
least one pixel in the area of interest,
identifying peaks in the time-dependent intensity curve
and
determining one or more of a frequency of the identified peaks and a maximum high of the identified
peaks,
generating one or more of a graphic representation of
the determined frequency and maximum high for the
at least one pixel and including the same in the peak
frequency map,
outputting the peak frequency map together with one or
more of the visible light image and the fluorescence
image, and
deriving a diagnostic result relative to the lymphatic
dysfunction, such as to lymphedema, such as relative to
a severity or level of the lymphatic dysfunction, such as
lymphedema, by analyzing the fluorescence image and
the peak frequency map.

The method of diagnosing lymphedema can be performed with higher preciseness and reliability and therefore can provide enhanced diagnostic results. The entirely new approach can replace the classical way of diagnosing lymphedema. The traditional way to diagnose lymphedema is to perform a manual inspection of the affected body part by a physician. This method is however inevitably influenced by the personal experience and qualification of the physician. The method of diagnosing lymphedema according to the above embodiment resolves this effect. Hence, the results can have a higher reproducibility and reliability.

The capturing of the fluorescence image and the capturing of the visible light image can be performed simultaneously, such as in absence of time-switching between a signal of the fluorescence image and a signal of the visible light image.

The fluorescent agent can be administered to an arm or leg of a patient by injecting the fluorescent agent in tissue between phalanges of the foot or hand of the patient.

Still further yet provided is a method of long-term therapy of lymphatic dysfunction, such as lymphedema, comprising:
performing a diagnosis relative to the lymphatic dysfunction, such as lymphedema by performing the previously mentioned method of diagnosing the lymphatic dysfunction, such as lymphedema, on a patient,
performing a therapy on the patient, the therapy being adjusted to the diagnostic result relative to the lymphatic dysfunction, such as lymphedema,
repeating the diagnosing of the lymphatic dysfunction, such as lymphedema, and performing a therapy on the patient, wherein in each iteration of the repeating, the therapy is adjusted to the diagnosis of the lymphatic dysfunction, such as lymphedema, such as to the severity or level of lymphatic dysfunction, such as lymphedema.

The method of long-term therapy can be useful because the diagnosis of lymphatic dysfunction, such as lymphedema, provides—in contrast to traditional methods—objective results with respect to the severity of the disease. The success of a long-term treatment therapy can be analyzed from an objective point of view. This can significantly enhance the therapy and the success of the therapy.

Still further provided is a method of providing a risk prediction value based on measuring of a fluorescence signal in a tissue of a body part, to which a fluorescent agent has been added, wherein the tissue to which the fluorescent agent has been added forms part of the body part, the method comprising:
capturing at least one fluorescence image in an area of examination by illuminating the tissue with excitation light having a wavelength suitable to generate emitted light by excited emission of the fluorescent agent and by spatially resolved measurement of the emitted light so as to provide the fluorescence image,
repeating the capturing of the fluorescence image to capture a plurality of fluorescence images over time so as to provide a time sequence of fluorescence images,
defining at least one calculation region in the at least one fluorescence image of the sequence of fluorescence images,
calculating a time-intensity curve from a signal intensity in the calculation region,
approximating the time-intensity curve by a model having at least one coefficient and determining the at least one coefficient that is related to an approximation of the model to at least a portion of the time-intensity curve;
providing the at least one coefficient to an input interface of a processor, wherein the processor comprises the input interface, an artificial intelligence (AI) model and an output interface, and wherein
the processor performs an inference operation by applying the at least one coefficient to the AI model and by generating a risk prediction value, which is indicative of a tissue perfusion in the calculation region, as output data at the output interface, from an output of the AI model, and
communicating the risk prediction value via a user interface.

The artificial intelligence model can enhance the analysis of the coefficients of the model, which can be applied for approximating the time-intensity curve. For example, the model can be fitted to the time intensity curve. Hence, the coefficients of the model can describe the best fit of the model to the shape of the time-intensity curve. Because the coefficients of the model are not directly linked to the underlying biological processes, it is often difficult for medical stuff to interpret these coefficients in a way to give them a meaning with respect to a medical indication, such as success of a treatment or future therapeutic measures. The artificial intelligence model can be trained to output a risk prediction value, which can be easy to interpret for medical stuff.

For this purpose, the artificial intelligence model, which can be, for example, a neural network, can be trained using training data for which the clinical outcome is known. The training data can be derived from a patient record. The neural network can be trained in supervised learning, wherein both types of supervised learning, classification and regression, can be applied. Regression is typically used for predicting of continuous output values and classification can be used for predicting certain classes of output. The continuous values and the classes are linked to the clinical outcome of the patient data, that can be used for training of the AI model.

According to an embodiment, the method can further comprise:
defining the calculation region, calculating the time-intensity curve, approximating the time-intensity curve by the model and determining the at least one coefficient, providing the at least one coefficient to an input interface of the processor, and the performing of the inference operation and the generating and outputting of the risk prediction value based on the AI model, are performed for a plurality of calculation regions, such as for every pixel or voxel of the fluorescence image, converting the risk prediction values across the plurality of calculation regions into a risk prediction value-derived image map, and outputting the risk prediction value-derived image map via the user interface.

The possibility to define certain calculation regions, which can be regions of interest, in which a tissue perfusion shall be analyzed, can be used because, for example in surgery or after a surgical procedure, certain critical regions of the surgical field can be analyzed. The full analysis of fluorescence images, which means an analysis on a pixel basis, gives the maximum possible information, but can be demanding with respect to computational power. The conversion of the risk prediction values into, for example, a color scale gives an easy to interpret image, which can be the risk prediction value-derived image map. This can be output or displayed in combination with a visible light image showing a surgical field.

Hence, the method can further comprise:

capturing at least one visible light image of a surface of the body part in the area of examination, wherein one or more of a viewing direction and a perspective of the fluorescence image and the visible light image are linked via a known relationship, and outputting the risk prediction value and the visible light image via the user interface.

Furthermore, the method can further comprise:

capturing at least one visible light image of a surface of the body part in the area of examination, wherein one or more of a viewing direction and a perspective of the fluorescence image and the visible light image are linked via a known relationship, and outputting the risk prediction value-derived image map as overlay image together with the visible light image via the user interface.

A direct link between the visible light image and the risk prediction values and the risk prediction value-derived image map, respectively, can be provided. This can simplify the assignment of certain findings, for example a certain risk prediction value, to a particular point or area in the surgical field.

According to still another embodiment, the capturing of the fluorescence image and the capturing of the visible light image can be performed simultaneously. The images can be acquired in the absence of time switching between a signal of the fluorescence image and a signal of the visible light image. Simultaneously capturing of the images can provide a direct link between fluorescence imaging and visible light imaging and the values, which can be derived from the fluorescence image, such as the risk prediction value. Because the images are captured at the same point in time, also highly dynamic areas of inspection can be analyzed.

According to still another embodiment, the model applied for approximating the time-intensity curve can be a single-tissue compartment model, such as the Adiabatic Approximation to the Tissue Homogeneity (AATH) model.

The AATH model can best describe the time-intensity curves. It can therefore be a very suitable model to predict the clinical outcome.

Furthermore, according to another embodiment, the artificial intelligence (AI) model can be a pre-trained neural network, such as a pre-trained neural network that was trained in supervised training on the basis of clinical patient data.

Training of the neural network on the basis of clinical patient data results in a AI model, which can give a high quality with respect to the confidence level of the risk prediction values. In other words, the training of the AI model can be important with respect to a confidence level of the risk prediction value.

Still further provided is a computer-based clinical decision support system (CDSS) for providing a risk prediction value based on a measurement of a fluorescence signal in a tissue of a body part, to which a fluorescent agent has been added, wherein the tissue to which the fluorescent agent has been added forms part of the body part, the CDSS comprising:

an illumination unit configured to illuminate the tissue with excitation light having a wavelength suitable to generate emitted light by excited emission of the fluorescent agent, a fluorescence imaging unit configured to capture at least one fluorescence image in an area of examination by illuminating the tissue with excitation light having a wavelength suitable to generate emitted light by excited emission of the fluorescent agent and by spatially resolved measurement of the emitted light so as to provide the fluorescence image, wherein the fluorescence imaging unit is further configured to capture a plurality of fluorescence images per time so as to provide a time sequence of fluorescence images, a processing device, which is configured to:
define at least one calculation region in the at least one fluorescence image of the sequence of fluorescence images, calculate a time-intensity curve from a signal intensity in the calculation region, approximate the time-intensity curve by a model having at least one coefficient and to determine the at least one coefficient that is related to an approximation of the model to at least a portion of the time-intensity curve;

provide the at least one coefficient to an input interface of a processor, wherein a processing device comprises the processor, which further comprises the input interface, an artificial intelligence (AI) model and an output interface, and perform an inference operation by applying the at least one coefficient to the AI model and by generating a risk prediction value, which is indicative of a tissue perfusion in the calculation region, as output data at the output interface, from an output of the AI model, and to communicate the risk prediction value to a user interface, wherein the CDSS further comprises the user interface, which is configured to display the risk prediction value.

For the CDSS, advantages which have been mentioned before with respect to the method of providing the restriction value, apply in a same or similar way. In view of this, they shall not be repeated.

The processing device can be configured to:
define the calculation region, calculate the time-intensity curve,
approximate the time-intensity curve by the model and to determine the at least one coefficient,
provide the at least one coefficient to an input interface of the processor, to perform the inference operation and to generate and output the risk prediction value based on the AI model, for a plurality of calculation regions, such as for every pixel or voxel of the fluorescence image,
convert the risk prediction values across the plurality of calculation regions into a risk prediction value-derived image map, and to communicate the risk prediction value-derived image map to the user interface,
wherein the user interface is configured to display the risk prediction value-derived image map.

Furthermore, the CDSS can further comprise:
a visible light imaging unit configured to capture at least one visible light image of a surface of the body part in the area of examination, wherein one or more of a viewing direction and a perspective of the fluorescence image and the visible light image are linked via a known relationship,
wherein the processing device can be further configured to output the risk prediction value and the visible light image to the user interface, and
the user interface can be configured to display the risk prediction value and the visible light image.

The CDSS can further comprise
a visible light imaging unit configured to capture at least one visible light image of a surface of the body part in the area of examination, wherein one or more of a viewing direction and a perspective of the fluorescence image and the visible light image are linked via a known relationship,
wherein the processing device can be further configured to output the risk prediction value-derived image map and the visible light image to the user interface, and
the user interface can be configured to display the risk prediction value-derived image map as overlay image together with the visible light image.

Furthermore, the fluorescence imaging unit and the visible light imaging unit can be configured to capture the fluorescence image and the visible light image simultaneously, such as in the absence of time-switching between a signal of the fluorescence image and a signal of the visible light image.

According to still another embodiment, the fluorescence imaging unit and the visible light imaging unit can be configured to capture the fluorescence image and the visible light image simultaneously. for example, the units can be configured to capture the respective images in absence of time switching between a signal of the fluorescence image and a signal of the visible light image.

According to still another embodiment, the processing device can comprise the model applied for approximating the time-intensity curve, which can be a single-tissue compartment model, such as the Adiabatic Approximation to the Tissue Homogeneity (AATH) model.

Furthermore, the processing device can comprise the artificial intelligence (AI) model, which can be a pre-trained neural network, such as a pre-trained neural network that was trained in supervised training on the basis of clinical patient data.

Still further provided is a combined method and a combined image capturing and processing device and computer-based clinical decision support system (CDSS).

Still further provided is a combined method of measuring a fluorescence signal and of providing a risk prediction value based on measuring of the fluorescence signal. This combined method comprises:
measuring a fluorescence signal in a tissue of a body part, to which a fluorescent agent has been added, and of imaging a surface of the body part, wherein the tissue to which the fluorescent agent has been added forms part of the body part,
capturing at least one fluorescence image in an area of examination by illuminating the tissue with excitation light having a wavelength suitable to generate emitted light by excited emission of the fluorescent agent and by spatially resolved measurement of the emitted light so as to provide the fluorescence image,
capturing at least one visible light image of a surface of the body part in the area of examination, wherein one or more of a viewing direction and a perspective of the fluorescence image and the visible light image are linked via a known relationship,
repeating the capturing of the fluorescence image to capture a plurality of fluorescence images over time so as to provide a time sequence of fluorescence images, wherein the repeating of the capturing of the visible light image to capture a plurality of visible light images can be over time so as to provide a time sequence of visible light images,
determining a peak frequency map for an area of interest in the fluorescence images by analyzing the time sequence of fluorescence images by:
  determining an time-dependent intensity curve of at least one pixel in the area of interest,
  identifying peaks in the time-dependent intensity curve and
  determining one or more of a frequency of the identified peaks and a maximum high of the identified peaks, and
  generating a graphic representation of one or more of the determined frequency and maximum high for the at least one pixel and including the same in the peak frequency map,
outputting the peak frequency map together with one or more of the visible light image and the fluorescence image,
providing of a risk prediction value comprising:
  defining at least one calculation region in the at least one fluorescence image of the sequence of fluorescence images,
  calculating a time-intensity curve from a signal intensity in the calculation region,
  approximating the time-intensity curve by a model having at least one coefficient and determining the at least one coefficient that is related to an approximation of the model to at least a portion of the time-intensity curve;
  providing the at least one coefficient to an input interface of a processor, wherein the processor comprises the input interface, an artificial intelligence (AI) model and an output interface, and
  performing an inference operation by applying the at least one coefficient to the AI model and by generating the risk prediction value, which is indicative of a tissue perfusion in the calculation region, as output data at the output interface, from an output of the AI model, and
communicating the risk prediction value via a user interface.

According to a further embodiment, the determining of the peak frequency map can further comprise the method mentioned as embodiments above. The providing of the risk prediction value can further comprise the methods mentioned as embodiments above.

In another embodiment, there is a combined image capturing and processing device and computer-based clinical decision support system (CDSS), wherein
the image capturing and processing device is configured to measure a fluorescence signal in a tissue of a body part, to which a fluorescent agent has been added, and to image a surface of the body part, wherein the tissue to which the fluorescent agent has been added forms part of the body part, the image capturing and processing device comprising an image capturing device, which comprises:
an illumination unit configured to illuminate the tissue with excitation light having a wavelength suitable to generate emitted light by excited emission of the fluorescent agent,
a fluorescence imaging unit configured to capture a fluorescence image in an area of examination by illuminating the tissue with excitation light having a wavelength suitable to generate emitted light by excited emission of the fluorescent agent, and by spatially resolved measurement of the emitted light so as to provide the fluorescence image,
a visible light imaging unit configured to capture a visible light image of a surface of the body part in the area of examination, wherein one or more of a viewing direction and a perspective of the fluorescence image and the visible light image are linked via a known relationship,
wherein the fluorescence imaging unit is further configured to capture a plurality of fluorescence images over time so as to provide a time sequence of fluorescence images, and
wherein the visible light imaging unit can be configured to capture a plurality of visible light images over time so as to provide a time sequence of visible light images,
the image capturing and processing device further comprising a processing device, which comprises:
a peak frequency map unit configured to determine a peak frequency map for an area of interest in the fluorescence images by analyzing the time sequence of fluorescence images, wherein the peak frequency map unit is configured to perform an analysis comprising:
determining an time-dependent intensity curve of at least one pixel in the area of interest,
identifying peaks in the time-dependent intensity curve,
determining a frequency of one or more of the identified peaks and a maximum high of the identified peaks, and
generating a graphic representation of one or more of the determined frequency and maximum high for the at least one pixel and including the same in the peak frequency map,
an output unit configured to output the peak frequency map together with one or more of the visible light image and the fluorescence image,
the computer-based clinical decision support system (CDSS) for providing of a risk prediction value based on a measurement of a fluorescence signal in a tissue of a body part, to which a fluorescent agent has been added, wherein the tissue to which the fluorescent agent has been added forms part of the body part, comprises:
an illumination unit configured to illuminate the tissue with excitation light having a wavelength suitable to generate emitted light by excited emission of the fluorescent agent,
a fluorescence imaging unit configured to capture at least one fluorescence image in an area of examination by illuminating the tissue with excitation light having a wavelength suitable to generate emitted light by excited emission of the fluorescent agent and by spatially resolved measurement of the emitted light so as to provide the fluorescence image,
wherein the fluorescence imaging unit is further configured to capture a plurality of fluorescence images over time so as to provide a time sequence of fluorescence images,
a processing device, which is configured to
define at least one calculation region in the at least one fluorescence image of the sequence of fluorescence images,
calculate a time-intensity curve from a signal intensity in the calculation region,
approximate the time-intensity curve by a model having at least one coefficient and to determine the at least one coefficient that is related to an approximation of the model to at least a portion of the time-intensity curve;
provide the at least one coefficient to an input interface of a processor, wherein a processing device comprises the processor, which further comprises the input interface, an artificial intelligence (AI) model and an output interface, and
perform an inference operation by applying the at least one coefficient to the AI model and by generating a risk prediction value, which is indicative of a tissue perfusion in the calculation region, as output data at the output interface, from an output of the AI model, and to communicate the risk prediction value to a user interface, wherein
the CDSS further comprises the user interface, which is configured to display the risk prediction value.

In the combined system, the image capturing and processing device and the CDSS can share the hardware of similar or identical units, for example the illumination unit, the fluorescence imaging unit, the visible light unit and the processing device.

According to a further embodiment, the image capturing and processing device can further comprise features mentioned as embodiments above. The CDSS can further comprise features mentioned as embodiments above.

The above embodiments can be linked in that they can provide enhanced solutions to perfusion analysis in a tissue of a body part. For example, enhanced perfusion analysis of the lymphatic fluid can be provided.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on exemplary embodiments, wherein reference is made expressly to the drawings with regard to the disclosure of all details that are not explained in greater detail in the text. In the drawings:

FIG. 16 illustrates a schematic illustration of a computer-based clinical decision support system (CDSS) for providing of a risk prediction value based on a measurement of a fluorescence signal.

In the drawings, the same or similar types of elements or respectively corresponding parts are provided with the same reference numbers in order to prevent the item from needing to be reintroduced.

DETAILED DESCRIPTION

Figure 1:
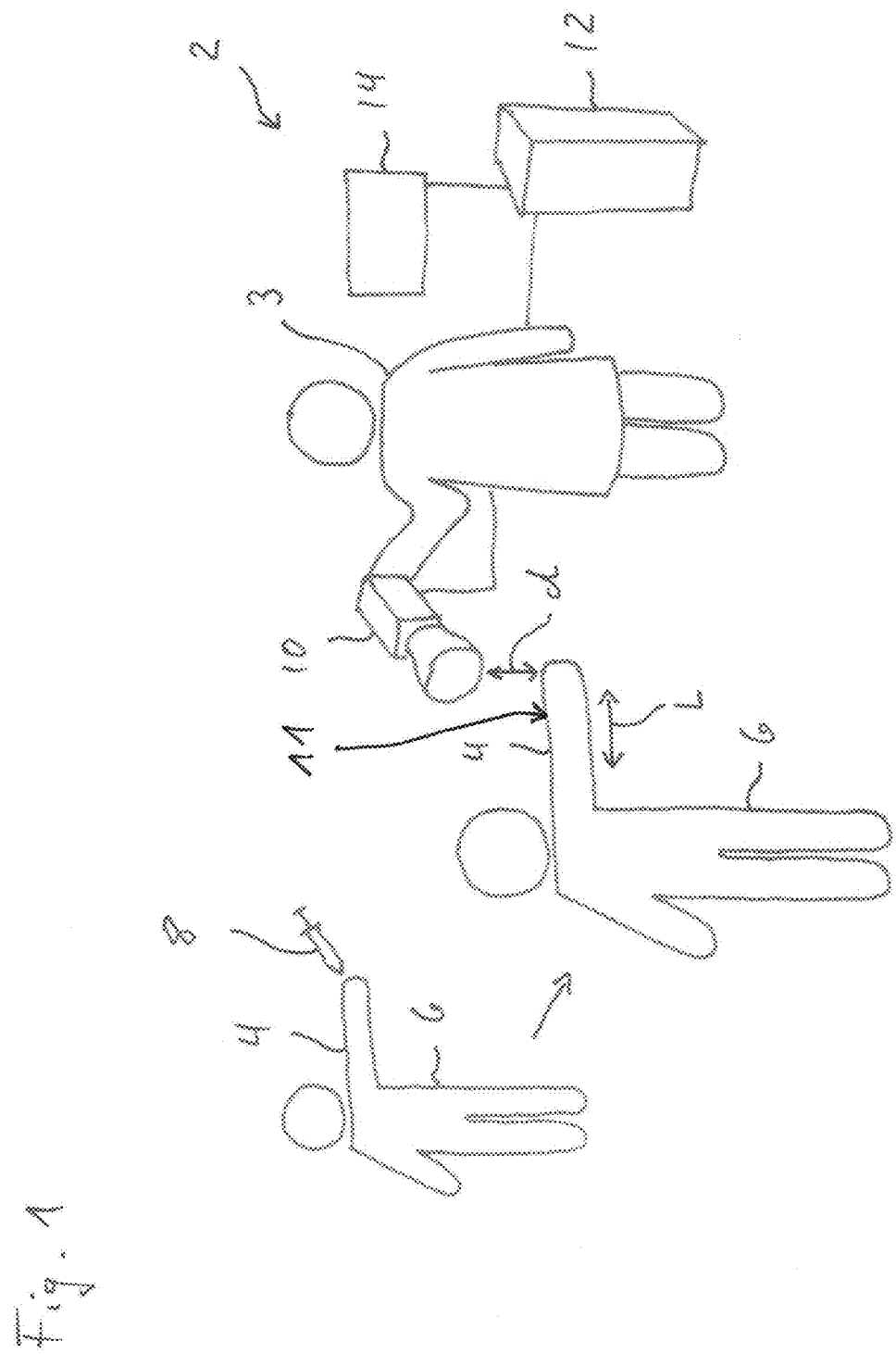
FIG. 1 illustrates a schematic illustration of an image capturing and processing device.

FIG. 1 illustrates an image capturing and processing device 2, which is configured to measure a fluorescence signal in a tissue of a body part 4 of a patient 6. By way of an example only, the body part 4 of the patient 6, which is inspected, is the arm. The measurement of the fluorescence signal can also be performed on other body parts 4 of the patient 6, for example the leg, a part of the head, the neck, the back or any other part of the body. The measurement can also be performed during open surgery. In this application scenario, the body part 4 can be for example an inner organ of the patient 6. The measurement of the fluorescent signal can also be performed during minimally invasive surgery. For this application scenario, the image capturing and processing devices 2 is at least partly integrated for example in an endoscope or laparoscope. For example, the endoscope or laparoscope comprises the image capturing device 10. Details of the endoscope will be explained further below.

Before the measurement initially starts, a fluorescent agent 8 is administered, i.e. injected, in the tissue of the patient's body part 4. The method for measuring a fluorescence signal in the tissue of the body part 4, which will also be explained when making reference to the figures illustrating the image capturing and processing device 2, excludes the administering of the fluorescent agent 8.

The fluorescent agent 8 is for example ICG. ICG (Indocyanine Green) is a green colored medical dye that is used for over 40 years. ICG emits fluorescent light when exited with near infrared light having a wavelength between 600 nm and 800 nm. The emitted fluorescence light is between 750 nm and 950 nm. Another suitable fluorescent agent 8 is methylene blue. It is also possible that the fluorescent agent 8 comprises two different medical dyes. For example, the fluorescent agent 8 can be a mixture of methylene blue and ICG.

Subsequent to the administration of the fluorescent agent 8, as it is indicated by an arrow pointing downwards right in FIG. 1, the patient's body part 4 is inspected using an image capturing device 10, which forms part of the image capturing and processing device 2.

The image capturing device 10 is configured to image a surface 11 of the body part 4 and to detect the fluorescence signal, which results from illumination of the fluorescent agent 8 with excitation light. When the image capturing device 10 is applied in surgery, the surface 11 of the body part 4 is a surface of for example an inner organ. In this case, the surface 11 of the body part 4 is identical to the surface of the tissue, to which the fluorescent agent 8 has been administered. For emission of light having a suitable excitation wavelength, the image capturing device 10 comprises an illumination unit 16 (e.g., a light source emitting the light having a suitable excitation wavelength) (not shown in FIG. 1).

The captured images are communicated to a processing device 12 (i.e., a processor comprising hardware, such as a hardware processor operating on software instructions or a hardware circuit), which also forms part of the image capturing and processing device 2. The results of the analysis are output, for example displayed on a display 14 of the processing device 12. The image capturing device 10 can be handled by a physician 3.

Figure 2:
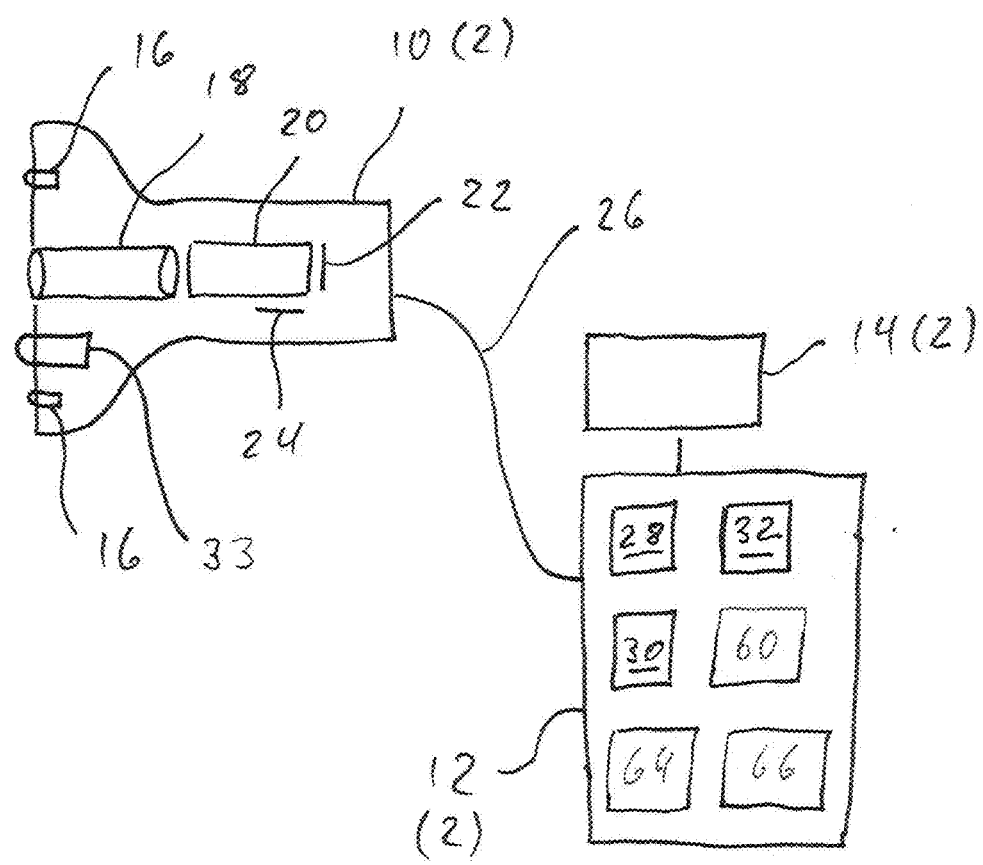
FIG. 2 illustrates a schematic illustration of an image capturing device and a processing unit of the imaging capturing and processing device.

FIG. 2 is a schematic illustration showing the image capturing device 10 and the processing unit 12 of the image capturing and processing device 2 in more detail. The image capturing device 10 comprises an illumination unit 16 which is configured to illuminate the tissue with excitation light having a wavelength suitable to generate fluorescent light by exciting emission of the fluorescent agent 8. For example, a plurality of LEDs is provided in the illumination unit 16.

The image capturing device 10 further comprises an objective lens 18 through which visible light and a fluorescence light are captured. Light is guided through the objective lens 18 to a prism assembly 20. The prism assembly 20 is configured to separate fluorescent light, which can be in a wavelength range between 750 nm and 950 nm, from visible light that results in the visible light image. The fluorescent light is directed on a fluorescence imaging unit 22, which is an image sensor, such as a CCD or CMOS sensor plus additional wavelength filters and electronics, if necessary. The fluorescence imaging unit 22 is configured to capture a fluorescence image by spatially resolved measurement of the emitted light, i.e. the excited emission of the fluorescent agent 8, so as to provide the fluorescence image. Furthermore, there is a visible light imaging unit 24, which can be another image sensor, such as a CCD or CMOS sensor plus an additional different wavelength filter and electronics, if necessary. The prism assembly 20 is configured to direct visible light on the visible light imaging unit 24 so as to allow the unit to capture the visible light image of a section of a surface 11 of the patient's body part 4. Similarly, the prism assembly 20 is configured to direct fluorescent light on the fluorescence imaging unit 22. The prism assembly 20, the fluorescence imaging unit 22 and the visible light imaging unit 24 will be explained in detail further below. The image data is communicated from the image capturing device 10 to the processing device 12 via a suitable data link 26, which can be a wireless datalink or a wired data link, for example a data cable.

The image capturing device 10 is configured in that the fluorescence imaging unit 22 and the visible light imaging unit 24 are operated to simultaneously capture the visible light image and the fluorescence image. The image capturing device 10 does not have to perform time switching between the signal of the fluorescence image and the signal of the visible light image. In other words, the sensors of the fluorescence imaging unit 22 and the visible light imaging unit 24 are exclusively used for capturing images in the respective wavelength range, which means that the sensors of the imaging units 22, 24 are used for either capturing a fluorescence image in the IR spectrum or for capturing a visible light image in the visible spectrum. The sensors 22, 24 are not used for capturing images in both wavelength ranges. This can result in significant advantages. For example, the sensors can be exactly positioned in focus, which is not possible when an image sensor is used for both purposes, i.e. to capture visible light and infrared light, because the focus point for these different wavelengths typically differ in position. Furthermore, the sensor parameters can be adjusted individually, for example with respect to a required exposure time or sensor gain. Individual settings can be used because IR signals are typically lower than visible light signals.

The fluorescence imaging unit 22 and the visible light imaging unit 24 have a fixed spatial relationship to each other. This is because the units are arranged in one single mounting structure or frame of the image capturing device 10. Furthermore, the fluorescence imaging unit 22 and the visible light imaging unit 24 use the same objective lens 18 and prism assembly 20 for imaging of the fluorescence image and the visible light image, respectively. Due to these measures, the fluorescence imaging unit 22 and the visible light imaging 24 are configured in that a viewing direction and a perspective of the fluorescence image and the visible light image are linked via a known and constant relationship. In the given embodiment, the viewing direction of the two images are identical because both units 22, 24 image via the same objective lens 18.

Figures 8A, 8B:
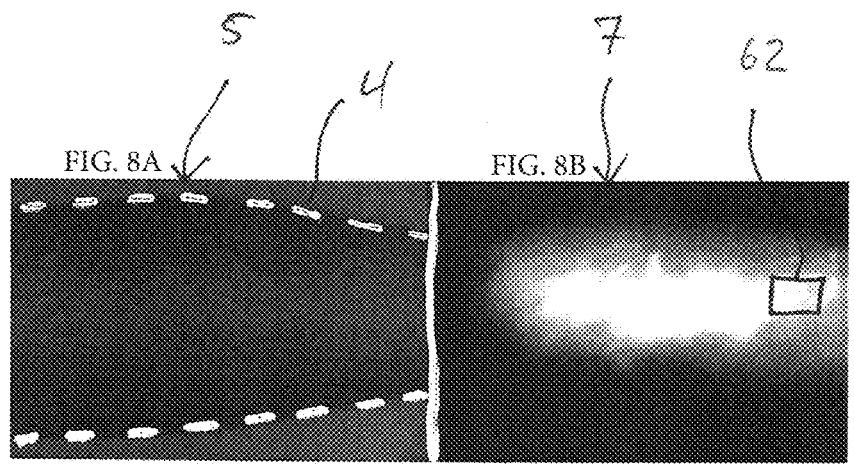

The fluorescence imaging unit 22 is further configured to capture a plurality of fluorescence images over time. In other words, a time sequence of fluorescence images is captured. This time sequence of fluorescence images is subsequently analyzed by a peak frequency map unit 60 (which can be a processor integral with or separate from the processing unit 12). For example, the peak frequency map unit 60 is a part of the processing device 12. The peak frequency map unit 60 is configured to determine a peak frequency map by analyzing the time dependent variation of the intensity of pixels in an area of interest in the time sequence of fluorescence images. The analysis comprises:

An area of interest is defined in the fluorescence images. This area of interest 62 can range from a single pixel of the fluorescence image to the full image. By way of an example, the area of interest is in-between these to two extrema. In FIG. 8b), there is a fluorescence image 7, in which a rectangular area of interest 62 is shown.

The peak frequency map unit 60 analyzes the intensity of the fluorescence signal in the area of interest 62. The intensity of all pixels in the area of interest 62 can be calculated. Based on this information, the peak frequency map unit 60 determines a time dependent intensity curve, which reflects the variation of the intensity of every pixel in the area of interest 62 over time.

Figure 3:
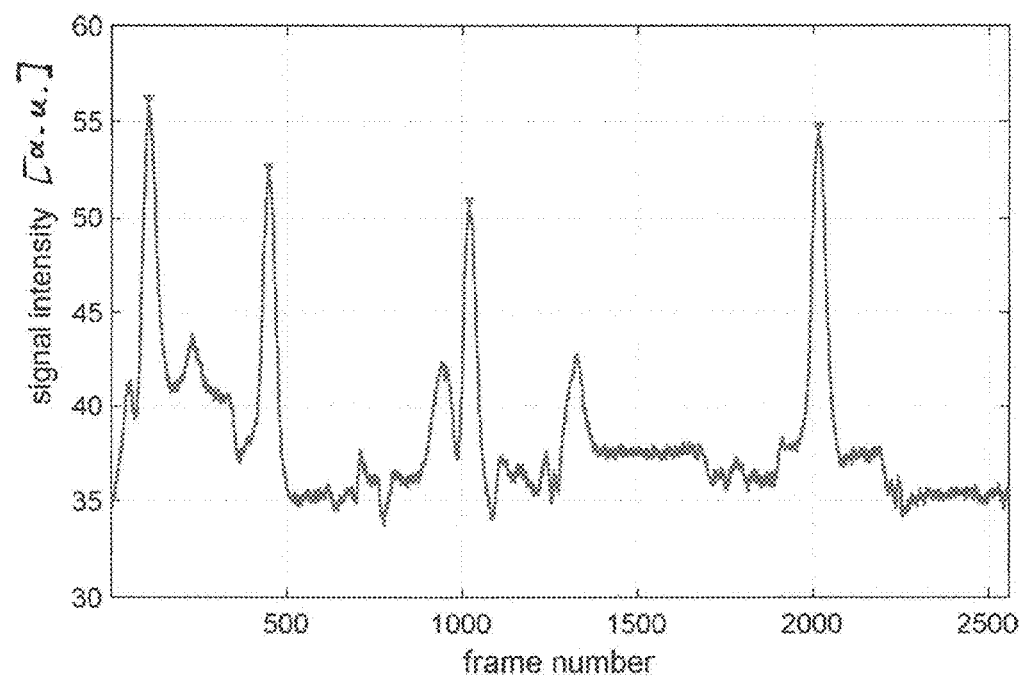
FIG. 3 illustrates a time-dependent intensity curve.

FIG. 3 shows the time dependent intensity curve for one arbitrary pixel in the area of interest 62. A signal intensity in arbitrary units is plotted against a frame number, which is equal to a time. By way of an example only, the time dependent intensity curve shows four major peaks being located at approx. frame No. 100, frame No. 450, frame No. 1,000 and frame No. 2,000. The peaks can be identified by slope analysis. It is also possible to consider every intensity value that is above a certain threshold a peak, for example all values above the threshold of intensity equal to 50. The exact location of the peak can again be determined by a slope analysis. The peaks are identified with respect to their position, in this case the frame number at which the peak is found, and by their maximum height, i.e. the maximum signal strength.

The peak frequency map unit 60 is further configured to determine a frequency of the identified peaks, which is a value for the number of peaks per unit time. The frequency of the peaks can be a value in units of for example peaks per 100 frames, peaks per 1,000 frames, peaks per second or any other suitable unit. Based on this information, a frequency of the identified peaks can be plotted in a graphic representation.

Figure 5:
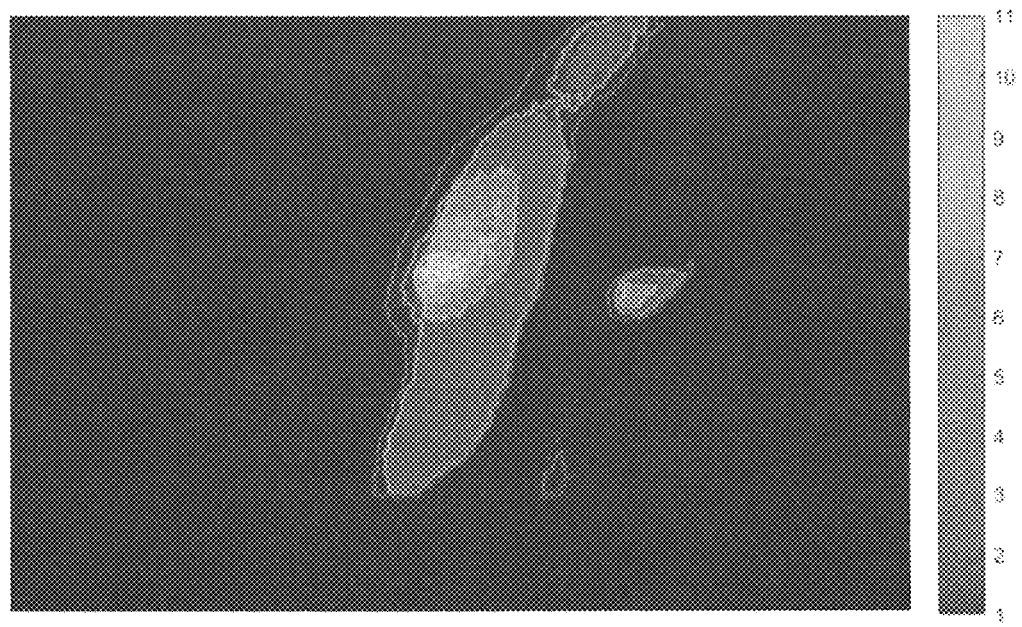
FIG. 5 illustrates a frequency map in false color plot.

FIG. 5 shows an illustration of a frequency map in false color plot. In this case, the area of interest was the entire fluorescence image, wherein the above described peak analysis was performed for every pixel of the fluorescence image. A frequency of identified peaks, which means a number of peaks per unit time, is coded by the color of the pixels. The frequency values can be binned in a number of classes or bins, to reduce the number of colors and to enhance the clarity of the plot. Pixels of the same or similar values are classified in one bin and continuous areas occupied by pixels in one bin can be surrounded by a margin line having the respective color. This is shown in FIG. 5. It is clearly visible that in the center of the depicted image, a high frequency of identified peaks can be found.

In a healthy lymphatic system, there is rhythmic transport of the lymphatic fluid in the lymphatic vessels. This process leads to oscillating intensity in the fluorescence images. If the rhythmic contraction of the vessels is fast, this results in a high frequency of peaks. This intensity oscillation can however only be found in certain areas of the fluorescence image, as it is visible in FIG. 5. These areas often correspond to the locations of the lymphatic vessels.

Figure 4:
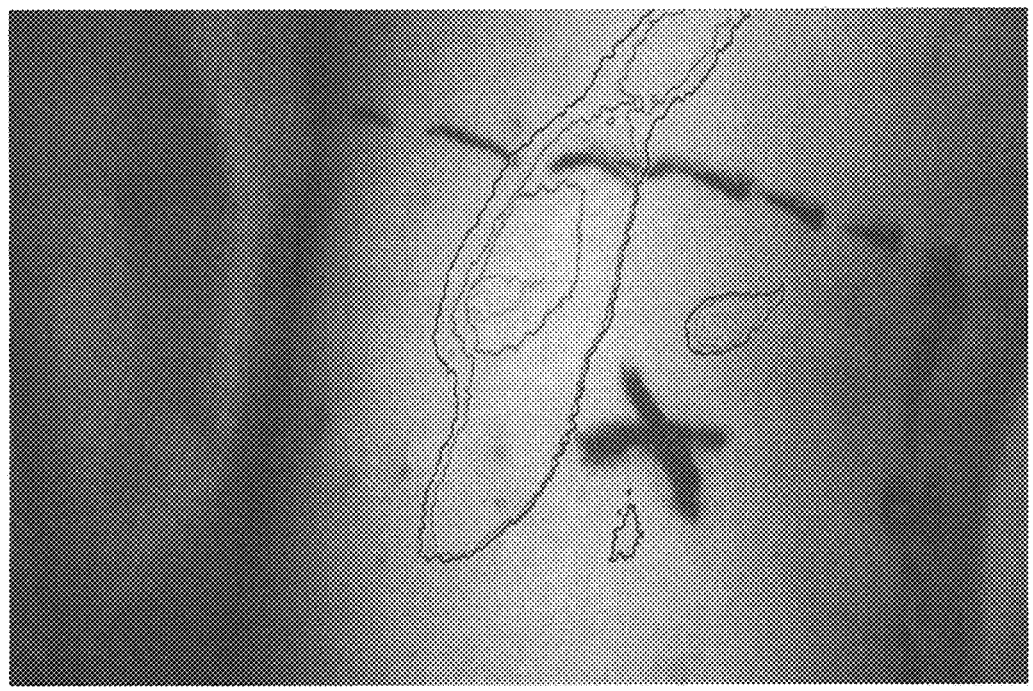
FIG. 4 illustrates an overly image of a visible light image and a frequency map.

The graphic representation of the determined frequency, namely the representation of the found frequency as false color plot (see FIG. 5) is generated by the peak frequency map unit 60. The peak frequency map is output via an output unit 64 and is for example displayed on the display 14 (such output unit can be a processor integral with or separate from the processing unit 12). The peak frequency map is output together with one or more of a visible light image 5 (see FIG. 8a) and together with a fluorescence image 7 (see FIG. 8b). Furthermore, the processing device 12 can comprise a superimposing unit 66 (which can be a processor integral with or separate from the processing unit 12) that is configured to superimpose the peak frequency map and a visible light image 5 so as to provide a peak/visible overlay image. This peak/visible overly image is shown in FIG. 4. The peak/visible overlay image can also be output by the output unit 64 on the display 14. The superimposing unit 66 can further be configured to compute an overlay image that is a combination of the peak frequency map (see FIG. 5) and the fluorescence image (see FIG. 8b).

In the embodiment, which was described with reference to FIGS. 3, 4 and 5, the peak frequency map is a frequency map. According to a further embodiment, which will be described with reference to FIGS. 3, 6 and 7, the peak frequency map is a maximum value map.

Figure 6:
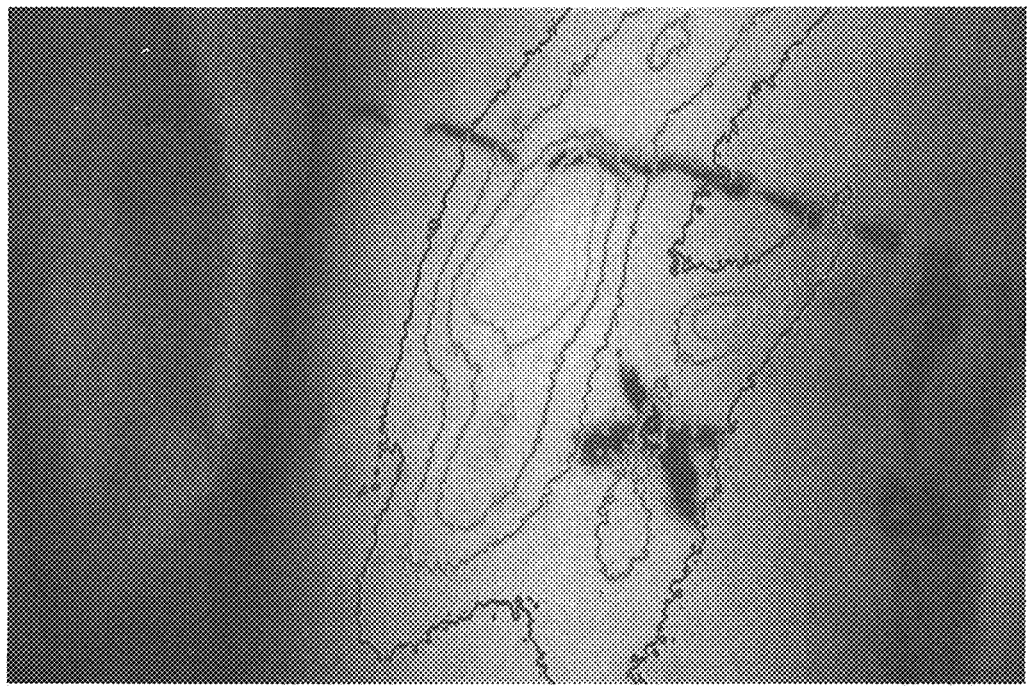
FIG. 6 illustrates an overly image of a visible light image and a maximum value map.
Figure 7:
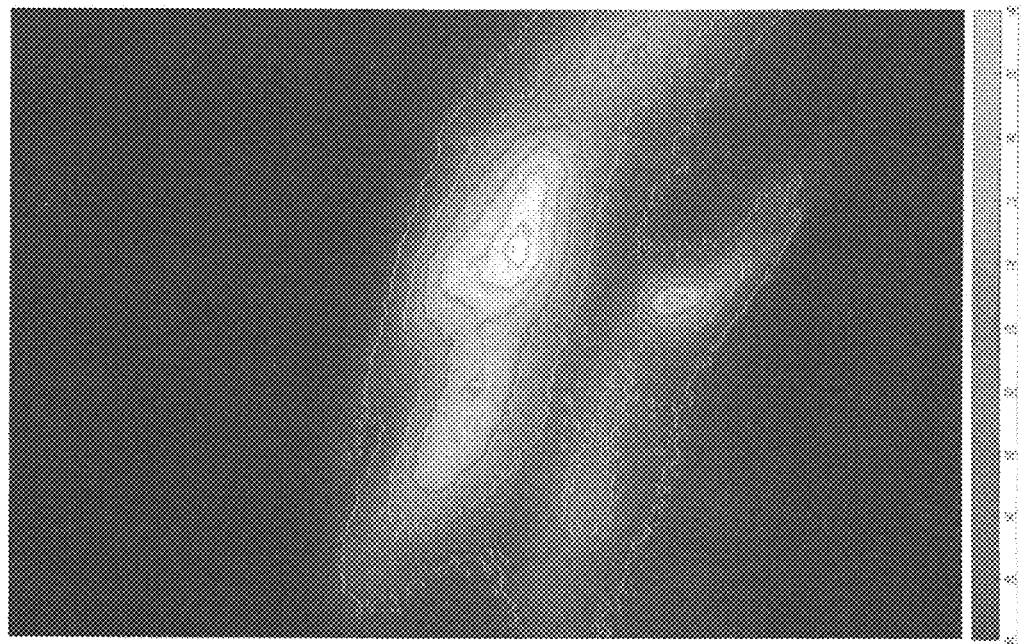
FIG. 7 illustrates a maximum value map in false color plot, FIG. 8a) illustrates an example of a visible light image and FIG. 8b) illustrates the corresponding fluorescence image.

For the determination of the maximum value map, the time dependent intensity curve, which is shown in FIG. 3, is analyzed with respect to a maximum height or value of the identified peaks. In other words, for every pixel in the area of interest 62 and maximum value for the signal intensity is determined. This information on the maximum height of the peaks is included in the maximum value map, which in this case represents the peak frequency map. A maximum value map is shown in false color plot in FIG. 7. The maximum value of the peaks is calculated for a respective one of the pixels in the fluorescence images, which means that the area of interest 62 comprises the full image. The maximum value map is calculated by the peak frequency map unit 60. It can be output by the output unit 64 together with the visible image 5 or the fluorescence image 7. Similar to the frequency map, also the maximum value map can be superimposed by the superimposing unit 66 with a visible light image. This is shown in FIG. 6. According to another embodiment, the maximum value map can be superimposed with a fluorescence image.

The image capturing device 10 is further configured to operate the fluorescence imaging unit 22 and the visible light imaging unit 24 to repeat the capturing of the fluorescence image and the visible light image so as to provide a series of fluorescence images and a series of visible light images. This operation can be performed by the processing device 12 operating the image sensor of the fluorescence imaging unit 22 and the image sensor of visible light imaging unit 24. The series of images is typically captured while an operator or physician 3 (see FIG. 1) moves the image capturing device 10 along a longitudinal direction L of the body part 4 of the patient 6. This movement can be performed in that subsequent images of the series of images comprise overlapping parts. In other words, details which are shown in a first image of the series of images are also shown in a subsequent second image of the series. This is important for the subsequent stitching process. To safeguard that corresponding features can be found in subsequent images, the frequency of image acquisition can be set to a sufficiently high value. The capturing of the images can be manually initiated by for example the physician 3 or the capturing of images can be controlled by the image capturing device 10 in that the described prerequisite is fulfilled.

The image capturing device 10 is configured it to capture the time series of fluorescence images. This time series should not be mixed up with the above referred is series of images that show different parts of the limb 4.

Once the two series of images (i.e. a first series of visible light images and a second series of fluorescence images showing different parts of the limb 4) or the series of image pairs (each image pair comprising a fluorescence image and a visible light image) are captured by the capturing device 10 and received in the processing device 12, the series of visible light images is processed by a stitching unit 28 (see FIG. 2) (which can be a processor integral or separate from the processing unit 12). The stitching unit 28 is configured to apply a stitching algorithm on the series of visible light images to generate a large visible light image of the body part 4. The large image is "larger" in that it shows a greater section of the body part 4 of the patient 6, which is analyzed with the image capturing device 10, then a single image.

The stitching algorithm starts with stitching of the visible light images. The stitching algorithm generates and applies a set of stitching parameters when preforming the stitching operation. The detailed operation of the stitching unit 28 will be described further below. The stitching unit 28 is configured to apply the stitching algorithm not only on the series of visible light images but also on the series of fluorescence images so as to generate a large fluorescence image. For the fluorescence images, a time series of fluorescence images is available. Furthermore, there is a series of fluorescence images comprising images that are captured at different parts of the limb 4. For the stitching of the fluorescence images, it can be a suitable approach to select only one fluorescence image or an average fluorescence image from the time series and it to use this image for the subsequent stitching process.

The stitching algorithm, which is applied for stitching of the fluorescence images is the same algorithm which is used for stitching of the visible light images. Furthermore, the stitching of the fluorescence images is performed using the same set of stitching parameters which was determined when performing the stitching of the visible light images. This is possible, because there is a fixed relationship between the viewing direction and perspective of the visible light images and the fluorescence images. Naturally, if the viewing direction and perspective of the visible light images and the fluorescence images are not identical, a fixed offset or a shift in the stitching parameters has to be applied. This takes into account the known and fixed spatial relationship between the IR and Vis image sensors and the corresponding optics.

Subsequent to the stitching, the large visible light image and the large fluorescence image are output. This output is supplemented with an output of the peak frequency map. For example, the images and the peak frequency map are displayed side-by-side on the display 14. Unlike traditional inspection systems, the display 14 shows a visible light image and a fluorescence image as well as a peak frequency map that correspond to each other. In other words, details that can be seen on the fluorescence image or the peak frequency map, for example a high fluorescence intensity or frequency that indicates an accumulation of lymphatic fluid or a high transport of lymphatic fluid. The respective position in the patient's body at which this takes place, can be found in the visible light image. This enables the physician 3 to exactly spot areas in which for example an accumulation of lymphatic fluid is present. This is very valuable information for example for a tailored and specific therapy of the patient 6.

It is also possible that the visible light image and the fluorescence image, such as the large visible light image and the large fluorescence image are superimposed so as to provide an overlay image, such as in a large overlay image, of the body part 4. This is also performed by a superimposing unit 30 of the processing device 12 (such superimposing unit can be a processor integral with or separate from the processing unit 12). The overlay image can also be output via the display 14.

FIG. 8a) shows an example of the visible light image 5, in which a section of a surface 11 of the body part 4 of the patient 6 is visible. By way of an example only, a section of the patient's leg is depicted. FIG. 8b) shows the corresponding fluorescence image 7 determined by measuring the fluorescence signal of the fluorescence agent 8, which has been applied to the patient's tissue in the leg. A high-intensity spot or area of the fluorescence signal is visible.

This strongly indicates an accumulation of lymph, which is due to a slow lymphatic transport and a possible lymphedema in the patient's leg. The physician 3 can now locate the area, in which the slow lymphatic transport takes place by comparing the fluorescence image 7 with the visible light image 5. In FIG. 8b), the area of interest 62 is indicated by the rectangle. The analysis of the time-dependent fluorescence intensity in this area 62 has been explained when making reference to FIGS. 3 to 7.

Figure 9:
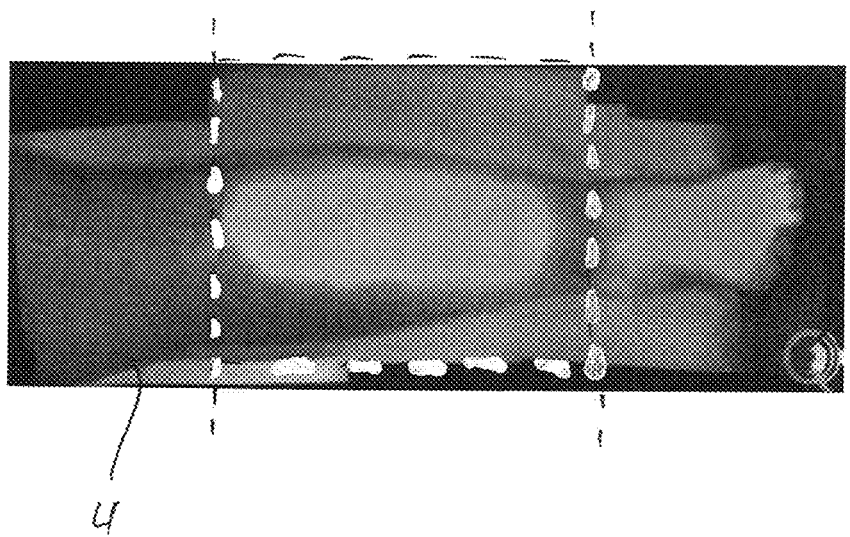
FIG. 9 illustrates a large overlay image, which is in part generated from the visible light and fluorescence images shown in FIGS. 8a) and 8b)

In FIG. 9, there is the overlay image 9 of the visible light image 5 and the fluorescence image 7. In addition to the images shown in FIGS. 8a) and 8b), stitching of the visible light images 5 and fluorescence images 7 has been performed. An exemplary single visible light image 5 and fluorescence image 7 can also be seen in FIG. 9, it respectively projects between the straight dashed lines shown in the large overlay image 9. By stitching together the visible light images 5 and the fluorescence images 7, the large overlay image 9 showing almost the entire body part 4 of the patient 6 can be provided. The fluorescence signal can be shown in false color so as to clearly distinguish from features of the visible light image 5.

Figure 10:
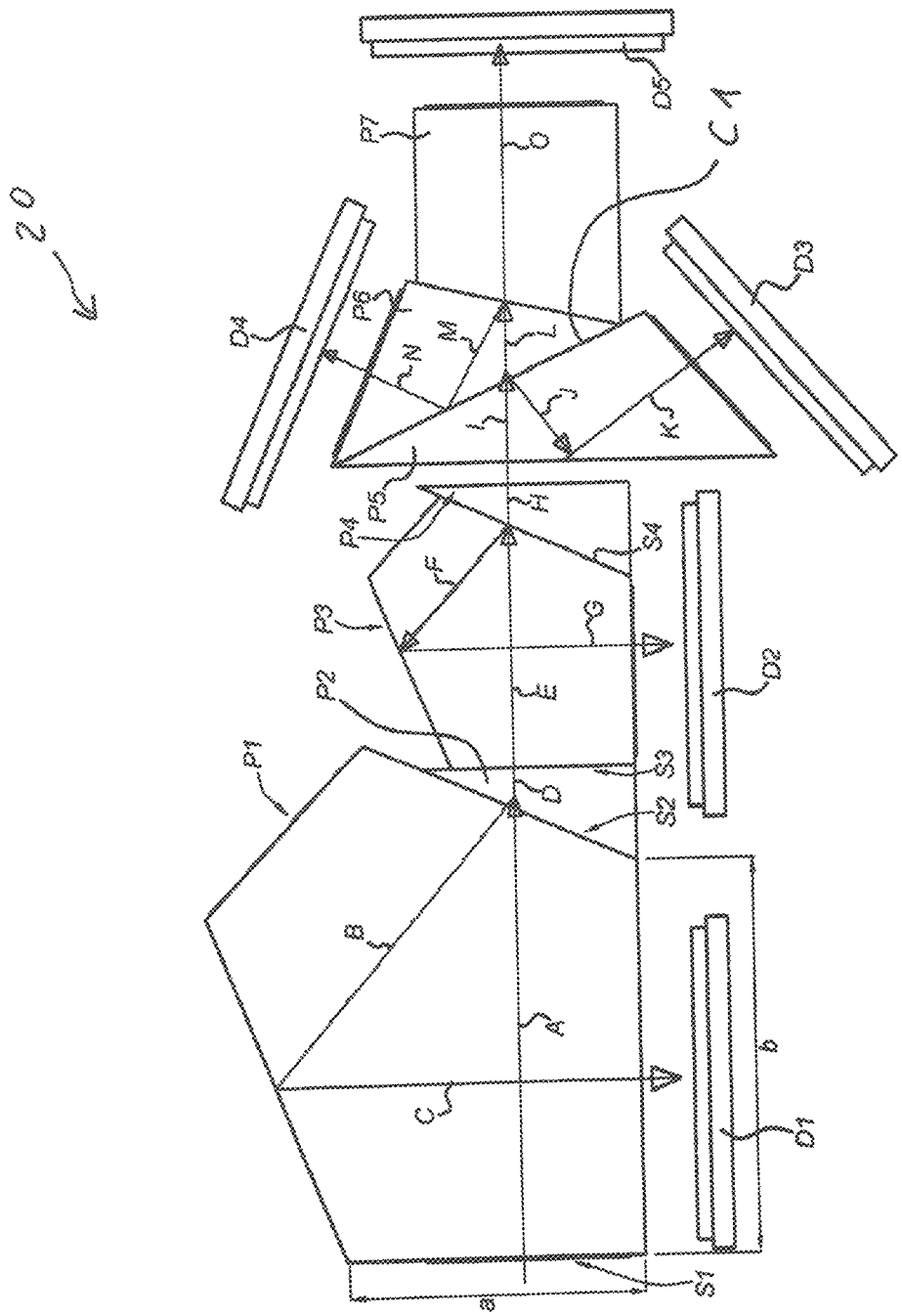
FIG. 10 illustrates a schematic illustration showing an internal prism assembly of the image capturing device.

In FIG. 10, there is an embodiment of the prism assembly 20 of the image capturing device 10. A first prism P1 is a pentagonal prism. The incoming light beam A, which is visible light and fluorescence light, enters the first prism P1 via the entrance face S1 and is partially reflected on face S2, being one of the two faces not adjoining the entrance face S1. The reflected beam B is then reflected against a first one of the faces adjoining the entrance face S1. The angle of reflection can be below the critical angle, so that the reflection is not internal (the adjoining face can be coated to avoid leaking of light and reflect the required wavelength of interest). The reflected beam C then crosses the incoming light beam A and exits the first prism P1 through the second one of the faces adjoining the entrance face S1, towards sensor D1. A part of the beam A goes through face S2 and enters compensating prism P2. Two non-internal reflections can be used to direct the incoming beam A via beams B and C towards the sensor D1. Furthermore, there can be no air gaps between prisms P1 and P2 and no air gaps between prisms P3 and P4 and no air gaps between prisms P2 and P3. Prism P2 is a compensator prism which is for adjusting the individual length of the light paths from the entrance face S1 to the sensors D1 . . . D5.

From P2, the beam D enters a second pentagonal prism P3. As in prism P1, inward reflection is used to make the beam cross itself. For brevity, the description of the beam will not be repeated, except to state that in prism P3, the beam parts E, F and G correspond to beam parts A, B and C in prism P1, respectively. Prism P3 can also not use internal reflection to reflect the incoming beam towards sensor D2. Two non-internal reflections can be used to direct the incoming beam E via beams F and G towards sensor D2.

After prism P3, there is another compensating prism P4. Finally, beam H enters the dichroic prism assembly comprising prisms P5, P6, and P7, with sensors D3, D4 and D5 respectively. The dichroic prism assembly is for splitting visible light in red, green and blue components towards respective sensors D3, D4 and D5. The light enters the prism assembly through beam I. Between P5 and P6, an optical coating C1 is placed and between prisms P6 and P7 another optical coating C2 is placed. Each optical coating C1 and C2 has a different reflectance and wavelength sensitivity. At C1, the incoming beam I is partially reflected back to the same face of the prism as through which the light entered (beam J). At that same face, the beam, now labelled K, is once again reflected towards sensor D3. The reflection from J to K is an internal reflection. Thus, sensor D3 receives light reflected by coating C1, and in analogue fashion sensor D4 receives light from beam L reflected by coating S2 (beams M and N), and sensor D5 receives light from beam O that has traversed the prism unhindered.

Between prism P4 and prism P5 there is an air gap. In the prism assembly 20, the following total path lengths can be defined for each endpoint channel (defined in terms of the sensor at the end of the channel):

Sensor D1 (e.g. first near infrared) path: A+B+C
Sensor D2 (e.g. second near infrared) path: A+D+E+F+G
Sensor D3 (e.g. red) path: A+D+E+H+I+J+K
Sensor D4 (e.g. blue) path: A+D+E+H+I+0
Sensor D5 (e.g. green) path: A+D+E+H+I+M+N The path lengths are matched, so that A+B+C=A+D+E+F+G=A+D+E+H+1+J+K=A+D+E+H+1+O=A+D+E+H+I+M+N.

The matching of path lengths can comprise an adjustment for focal plane focus position differences in wavelengths to be detected at the sensors D1-D5. That is, for example the path length towards the sensor for blue (B) light may not be exactly the same as the path length towards the sensor for red (R) light, since the ideal distances for creating a sharp, focused image are somewhat dependent on the wavelength of the light. The prisms can be configured to allow for these dependencies. D+H lengths can be adjusted and act as focus compensators due to wavelength shifts, by lateral displacement of the compensator prisms P2, P4.

A larger air gap in path I can be used for additional filters or filled with a glass compensator for focus shifts and compensation. An air gap needs to exist in that particular bottom surface of red prism because of the internal reflection in the path from beam J to beam K. A space can be reserved between the prism output faces and each of the sensors D1-D5 to provide an additional filter, or should be filled up with glass compensators accordingly.

The sensors D1 and D2 are IR sensors, configured for capturing the fluorescence image 7. By way of an example, the sensors D1 and D2 plus suitable electronics are a part of the fluorescence imaging unit 22. The sensors D3, D4 and D5 are for capturing the three components of the visible light image 5. By way of an example, the sensors D3, D4 and D5 plus suitable electronics are a part of the visible light imaging unit 24. It is also possible to consider the corresponding prisms that direct the light beams on the sensors, a part of the respective unit, i.e. the fluorescence imaging unit 22 and the visible light imaging unit 24, respectively.

Figure 11:
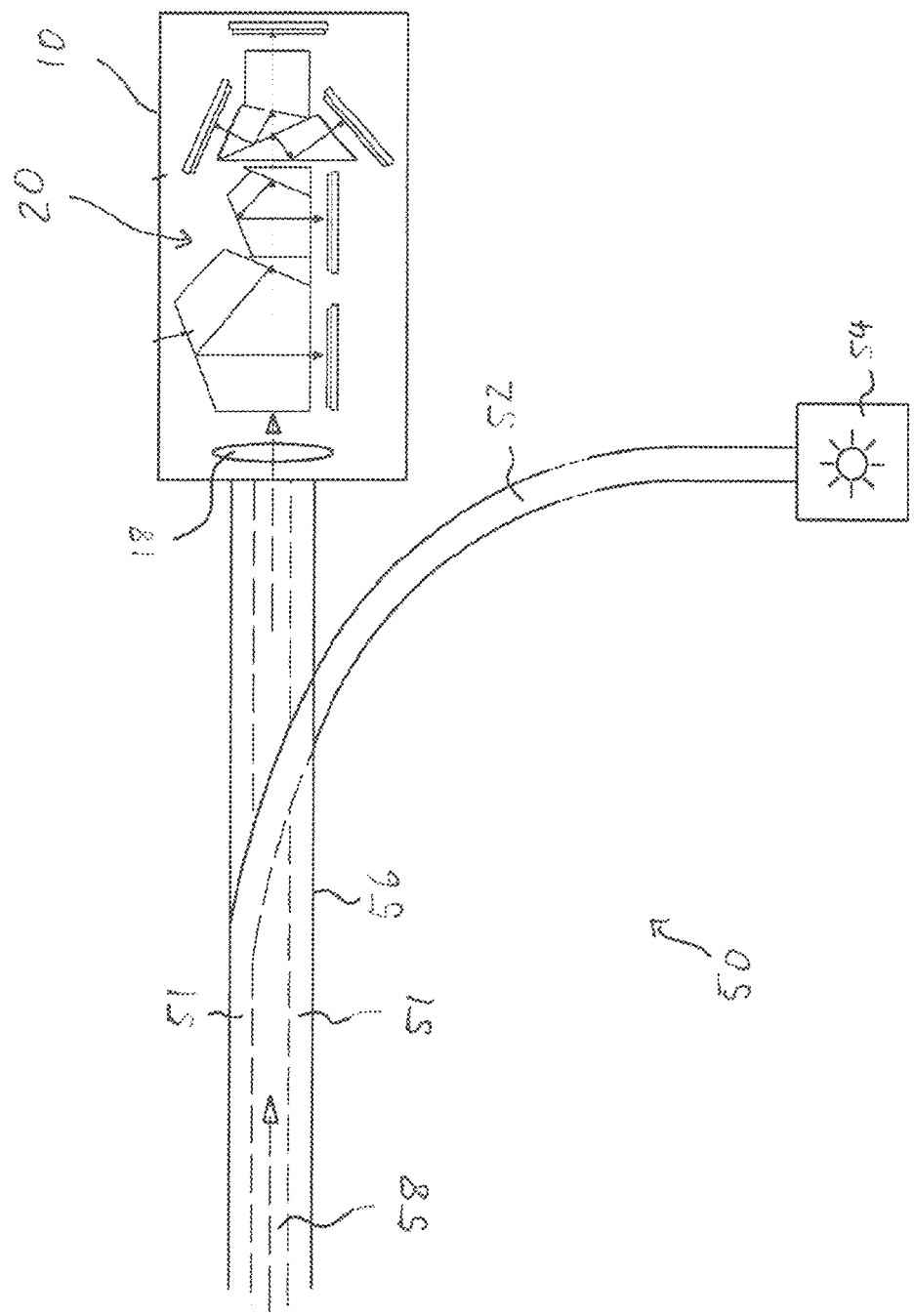
FIG. 11 illustrates a schematic illustration of an endoscope or laparoscope including the image capturing device.

FIG. 11 schematically shows an endoscope 50 or laparoscope, according to an embodiment. The differences between laparoscopes and endoscopes are relatively small, when considering the aspects. Hence, where the description mentions an endoscope, a laparoscope configuration is usually also possible. By way of an example only, in the following, reference will be made to an endoscope 50.

The endoscope 50 comprises an image capturing device 10 that has been explained in further detail above. The image capturing device 10 comprises an objective lens 18 through which the fluorescent light image 7 and the visible light image 5 are captured. The objective lens 18 focuses the incoming light through the entrance face S1 of the prism assembly 20 on the sensors D1 to D5. The objective lens 18 can also be integrated in the last part of the endoscope part to match the prism back focal length.

The endoscope 50 comprises an optical fiber 52 connected to a light source 54 that couples light into the endoscope 50. The light source 54 can provide white light for illumination of the surface 11 of the body part 4 and for capturing of the visible light image 5. Furthermore, the light source 54 can be configured to emit excitation light which is suitable to excite the fluorescent dye that is applied as the fluorescent agent to emit fluorescence light. In other words, the light source 54 can be configured to emit both, visible light and light in the IR spectrum.

Inside a shaft 56 of the endoscope 50, the optical fiber 52 splits off into several fibers 51. The endoscope 50 can have a flexible shaft 56 or a rigid shaft 56. In a rigid shaft 56, a lens system consisting of one or more of lens elements and relay rod lenses can be used to guide the light through the shaft 56. If the endoscope 50 has a flexible shaft 56 the fiber bundle 51 can be used for guiding the light of the light source 54 to the tip of the endoscope shaft 56. For guiding light from the distal tip of the endoscope shaft 56 (is not shown in FIG. 6) coming from a field of examination to the image capturing device 10 at the proximal end of the shaft 56, a fiber bundle 58 is arranged in the shaft 56 of the endoscope 50. In another embodiment, which is not shown in the figure, the entire image capturing device 10 can be miniaturized and arranged at a distal tip or end of the endoscope shaft 56.

Figure 12:
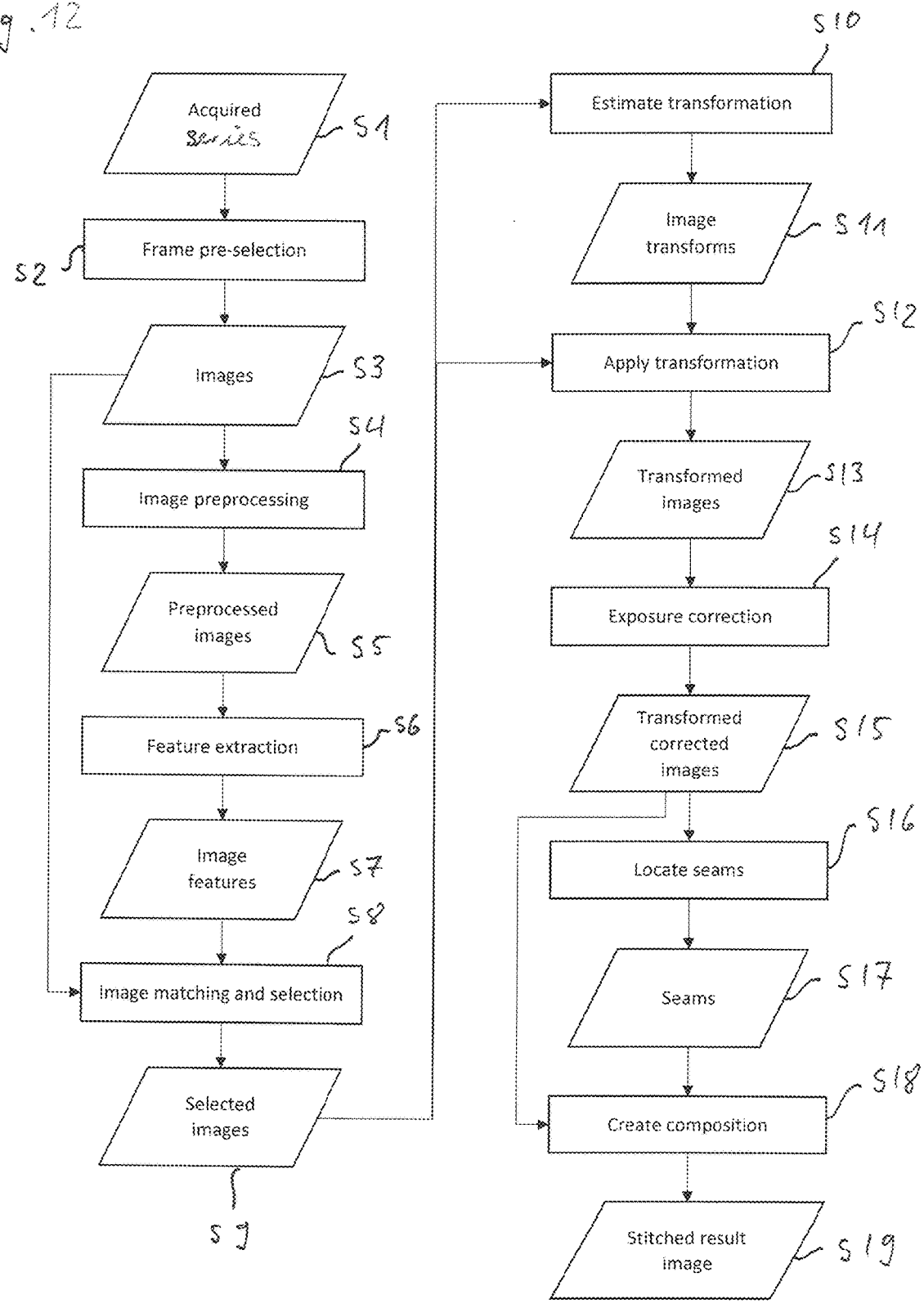
FIG. 12 illustrates a flowchart of a stitching algorithm.

FIG. 12 shows a flowchart of the stitching algorithm, which can be used for stitching of the visible light images and the fluorescence images. The flow chart is more or less self-explanatory and will be very briefly described. Firstly, the acquired series of images (S1) is forwarded to the stitching unit 24 of the processing device 12. The algorithm then performs a frame preselection (S2). In this preselection, frames suitable for stitching are selected. S3 represents the selected images to be stitched, they then undergo preprocessing (S4). In the preprocessed images (S5) a feature extraction is performed (S6). When the image features have been extracted (S7), image matching (S8) is performed using the images known from S3 and the extracted features from S7. Based on the selected images (S9) a transformation of the images is estimated (S10). This estimate of image transformation (S11), also referred to as stitching parameters, is applied (S12). The application of the transformation results in transformed images (S13). A further image correction can be performed, for example an exposure correction (S14). The transformed and corrected images (S15) are stitched together by locating seams (S16), i.e. lines along which the images are joined together. The data indicating the location of the seams (S17) is used together with the transformed and corrected images (S12) to create a composition of images (S18). In the given embodiment, this results in the large visible light image or the large fluorescence image, as the stitching results (S19).

Furthermore, the image capturing device 10, which is applied for capturing the visible light images 5 and the fluorescence images 7 can further comprise a distance sensor 33 that communicates with a measurement unit 32 which is located in the processing device 12 (such measurement unit can be a processor integral with or separate from the processing unit 12). The distance sensor 33 is configured to measure a distance d (see FIG. 1) between the surface 11 of the patient's body part 4, which is captured in the visible light image 5, and the image capturing device 10. The distance sensor 33, which communicates with the measurement unit 32, is for example an ultrasonic sensor, a laser distance sensor or any other suitable distance measurement device. Furthermore, the image capturing device 10 is configured to output a signal, which is indicative of the measured distance d. For example, the image capturing device 10 outputs an optical or acoustical signal giving the operator of the device 10 information on a best distance d for performance of the measurement. Performing the measurement with constant distance d significantly enhances the measurement results, because there is inter alia a homogeneous illumination.

Figure 13:
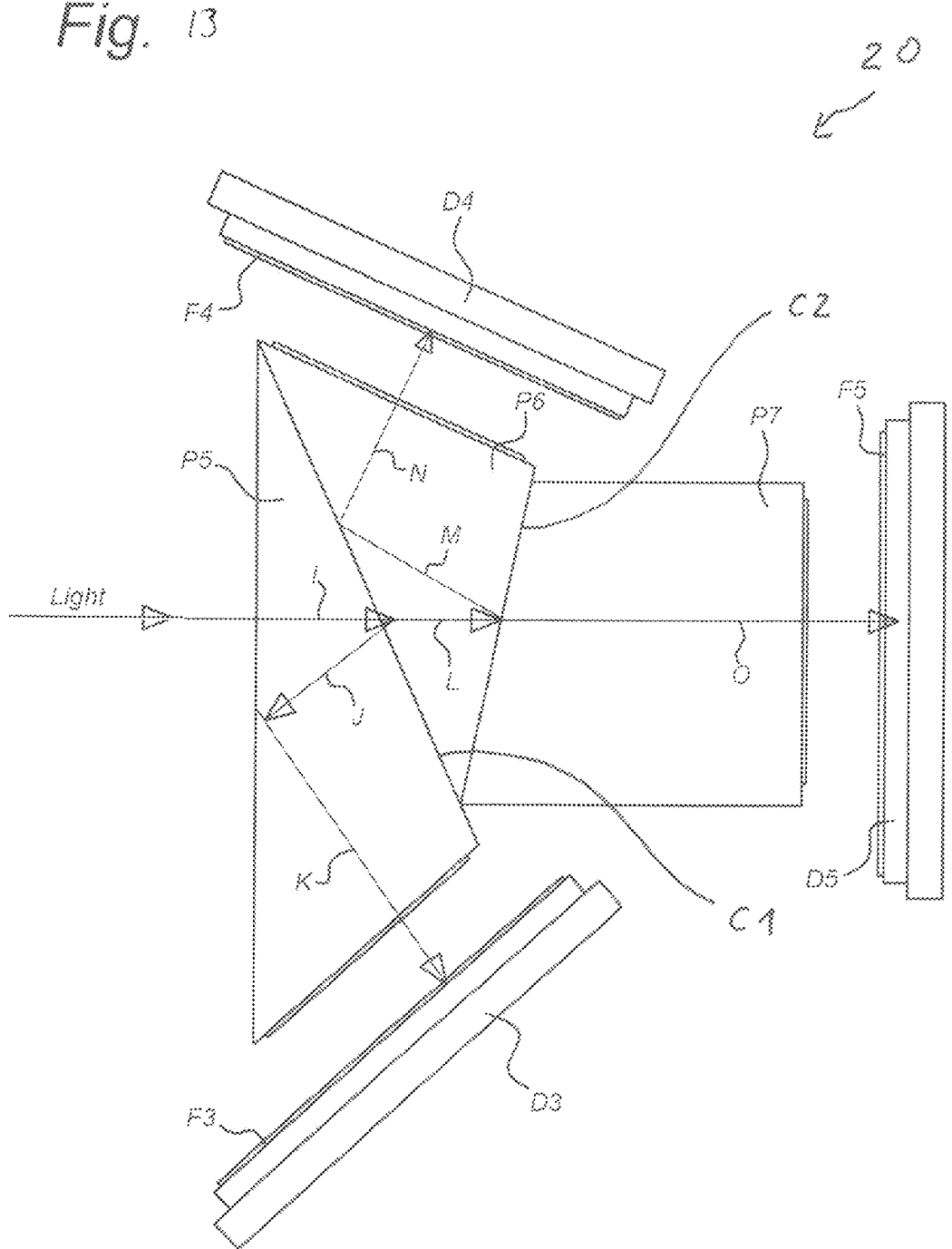
FIG. 13 illustrates a schematic illustration showing another internal prism assembly of the image capturing device.

In FIG. 13, there is an embodiment of another prism assembly 20 of the image capturing device 10. The prism assembly 20 comprises prisms P5, P6, and P7, which, for example, are configured for splitting light in red, green and blue components towards respective sensors D3, D4, and D5. According to a further embodiment, the prism assembly 20 is configured to split incoming light in a green component, a red/blue component and an infrared component and to direct these towards the respective sensors D3, D4, and D5. According to still another embodiment, the prism assembly 20 is configured to split incoming light in a visible light component, which is directed to a red/green/blue sensor (RGB sensor), a first infrared component of a first wavelength or wavelength interval and a second infrared component of a second wavelength or wavelength interval, and to direct these towards the respective sensors D3, D4, and D5.

The light enters the prism assembly 20 through the arrow indicated. Between P5 and P6, an optical coating C1 is placed and between prisms P6 and P7 an optical coating C2 is placed, each optical coating C1 and C2 having a different reflectance and wavelength sensitivity. At C1, the incoming beam I is partially reflected back to the same face of the prism P5 as through which the light entered (beam J). At that same face, the beam, now labelled K, is once again reflected towards filter F3 and sensor D3. The reflection from J to K is an internal reflection. Thus, filter F3 and sensor D3 receive light reflected by coating C1, and in analogue fashion filter F4 and sensor D4 receive light from beam L reflected by coating S2 (beams M and N). Filter F5 and sensor D5 receive light from beam O that has traversed the prisms unhindered.

When making reference to the embodiment in which the incoming light is split up in a red, green and blue component, the coatings and filters are selected accordingly.

In the embodiment, in which the incoming light is separated in a green component, a red/blue component and an infrared component, the filter F3 can be a patterned filter (red/blue). There can be an array of red and blue filters in an alternating pattern. The pattern can consist of groups of 2×2 pixels, which are filtered for one particular color. Filter F4 can be a green filter, which means the filter comprises only green filters. There is a single pixel grid with the light received at each pixel being filtered with a green filter. Filter F5 can be an IR filter. Each pixel is filtered with an IR filter.

In general, the coatings C1, C2 should match the filters F3, F4, F5. For example, the first coating C1 may transmit visible light while reflecting IR light, so that IR light is guided towards IR filter F3. The second coating C2 may be transparent for green light while reflecting red and blue light, so that filter F4 should be the red/blue patterned filter and F5 should be the green filter 23.

According to the further embodiment, in which in incoming light is split up in the visible light component (RGB), the first infrared component and the second infrared component, the coatings C1, C2 and the filters F3, F4, F5 are configured in that for example the sensor D4 is a color sensor (RGB sensor) for detecting the visible light image in all three colors. Furthermore, the sensor D3 can be configured for detecting fluorescence light of the first wavelength and the sensor D5 is configured for detecting fluorescence light of the second wavelength.

Similarly, when making reference to the prism assembly 20 in FIG. 10, the coatings S1, S2, S3, S4, C1 and C2 as well as the filters F1, F2, F3, F4 and F5, which are arranged in front of a respective one of the sensors D1, D2, D3, D4 and D5, can be configured in that up to four fluorescence light wavelengths can be detected. For example, the sensor D4 is a color sensor for detecting the visible light image in all three colors. The sensor D3 is for detecting fluorescence light of a first wavelength or wavelength interval, the sensor D5 is for detecting fluorescence light of a second wavelength or wavelength interval, the sensor D1 is for detecting fluorescence light of a third wavelength or wavelength interval, and the sensor D2 is for detecting fluorescence light of a fourth wavelength or wavelength interval.

The image capturing and processing device 2, which is described above in connection with FIGS. 1 and 2, can also be applied to measure a fluorescence signal, from which a time-intensity curve can be derived or calculated.

In the following, a method of providing a risk prediction value based on a measurement of a fluorescence signal will be explained. The fluorescence signal is detected in a tissue of a body part 4, to which a fluorescent agent 8 has been added, wherein the tissue, to which the fluorescent agent 8 has been added, forms part of the body part 4.

At least one fluorescence image 7 is captured. The fluorescence image 7 is captured in an area of examination by illuminating the tissue with excitation light having a wavelength suitable to generate emitted light by excited emission of the fluorescent agent 8. A spatially resolved measurement of the emitted light is performed to provide the fluorescence image 7. The capturing of the fluorescence image 7 is repeated to capture a plurality of fluorescence images 7 over time and to provide the time sequence of fluorescence images 7. At least one calculation region 80 is defined in the at least one fluorescence image 7 of the sequence of fluorescence images 7. In this calculation region 80, a time-intensity curve is calculated from the signal intensity in the calculation region 80.

Figure 14:
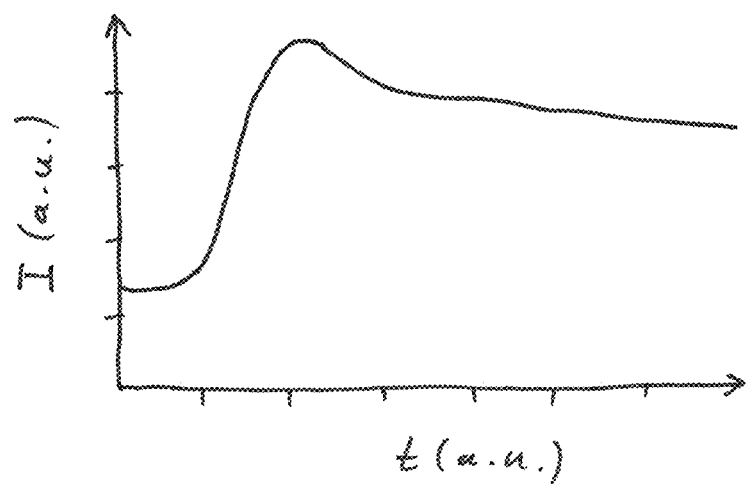
FIG. 14 illustrates a time intensity curve of a fluorescence signal.
Figure 15:
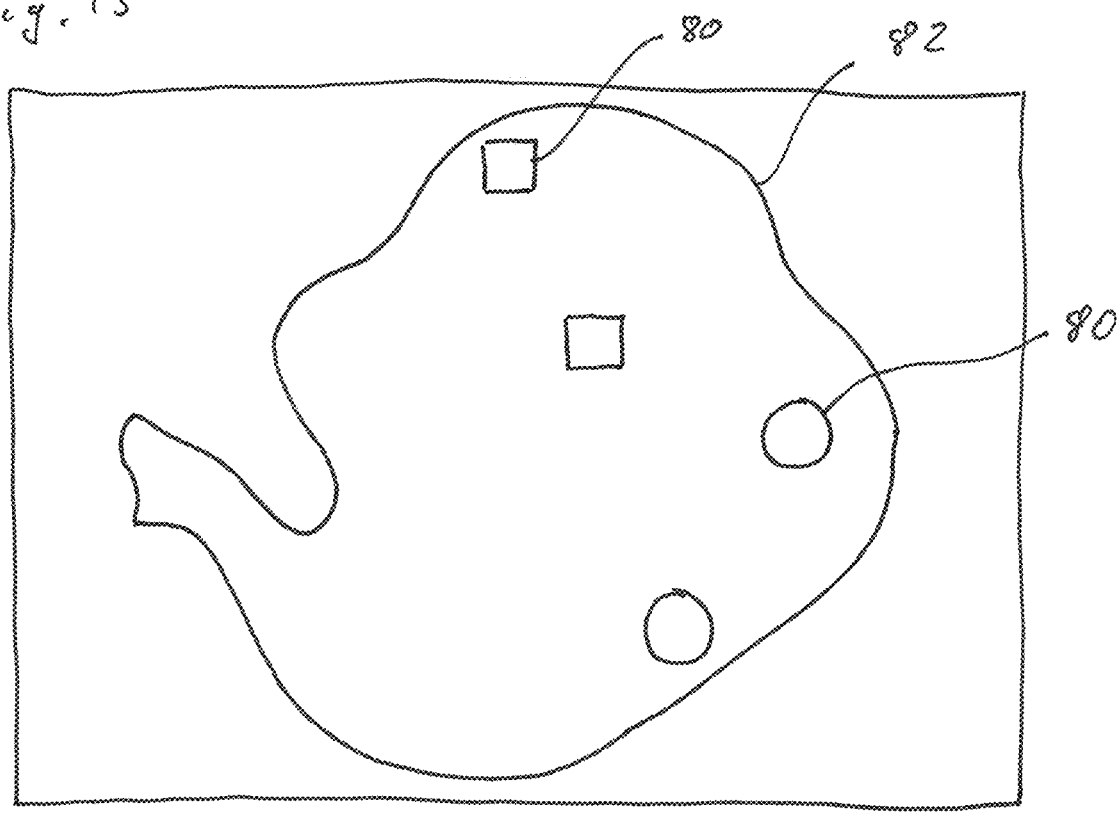
FIG. 15 illustrates a schematic illustration of an area of examination, in which calculation regions have been defined.

FIG. 14 shows a time-intensity curve of a signal intensity in a calculation region 80. FIG. 15 shows a schematic illustration of an area of examination, in which certain calculation regions 80, only some of which are given reference numerals, are indicated. In the area of examination, there is an exemplary organ 82, on which a surgical procedure has been performed. For risk assessment of the surgical procedure, certain calculation regions 80 are defined, in which perfusion measurements should be performed. In other words, at least one time-intensity curve, which is in principle depicted in FIG. 14, can be calculated from a respective one of the calculation regions 80.

The time-intensity curve is approximated by a model having at least one coefficient. The model applied for approximation of the time-intensity curve is, for example, a single tissue compartment model. The Adiabatic Approximation to the Tissue Homogeneity (AATH) model can be best suited for approximating the time-intensity curve. The result of the modelling of the time-intensity curve is a best fit of the model to the shape of the time-intensity curve at least in a certain region or segment. From this best fit, the at least one coefficient of the model can be determined.

The at least one coefficient of the model is provided to an input interface of a processor 84 (i.e., a processor comprising hardware, such as a hardware processor operating on software instructions or a hardware circuit), which forms part of a processing device 92. The processing device 92, which can be the same or different from processing device 12, and which is for example a computer, a medical device or can be even implemented in a computing cloud, is a part of a computer-based clinical decision support system (CDSS). This is schematically illustrated in FIG. 16.

The CDSS 86 comprises an image capturing device 10, which is explained in detail in FIG. 2. The relevant input features are the at least one coefficient of the model, which is fit to the time-intensity curve. The coefficient(s) is/are communicated to the input interface of the processor 84, wherein the $1^{st}$ to $N^{th}$ input feature are the coefficients 1 to N of the model used for fitting the time-intensity curve. The processor 84 holds an AI model, for example a neural network. The processor 84 performs an inference operation by applying the at least one coefficient as input features to the AI model. The output of the AI model, which means the output predicted from the AI model inference operation, is the risk prediction value. The risk prediction value can be communicated together with a confidence score to a user interface 88.

At the user interface 88, a risk prediction value for a certain calculation region 80 can be displayed. Furthermore, for example a visible light image 5 showing the organ 82, the calculation regions 80 and associated risk values can be displayed. Furthermore, for every pixel of the fluorescence image 7, a risk prediction value can be calculated. This plurality of risk prediction values can be converted into a prediction value-derived image map. This image map can also be communicated via the user interface 88, for example as an overlay image to a visible light image.

The fluorescence image 7 and the visible light image 5 can be captured simultaneously, for example using an image-capturing device comprising a prism configuration like shown in FIG. 10, 11 or 13.

The AI model can be a pre-trained neural network. This neural network can be trained using data of patient records 90 taken from a database. The patient records 90 comprise a clinical outcome of, for example, a certain surgery. By this measure, time-intensity curves and risk prediction values are linked to a certain clinical outcome. These patient records can be used for supervised training of the neural network, which can be implemented as an AI model in the processor 84. The processing device 92 can further include the image capturing device 10 and the user interface 88. It can optionally also include the database comprising the patient records 90.

In FIG. 16, there is a schematic diagram of an exemplary computer-based clinical decision support system (CDSS) that is configured to provide the risk prediction value based on the at least one coefficient of the model applied for approximation of the time intensity curve, which is supplied at inference. In various embodiments, the CDSS 86 includes the input interface through which the at least one coefficient, which is specific to a patient is provided as an input feature to the artificial intelligence (AI) model, the processor 84, which performs the inference operation in which the at least one coefficient is applied to the AI model to generate the risk prediction value, and the user interface (UI) 88 through which the risk prediction value is communicated to a user, e.g., a clinician.

In some embodiments, the input interface may be a direct data link between the CDSS 86 and one or more medical devices, for example the image capturing device 10, that generate at least some of the input features. For example, the input interface may transmit the input feature(s) directly to the CDSS 86 during one or more of a therapeutic and diagnostic medical procedure. Additionally, or alternatively, the input interface may be a classical user interface that facilitates interaction between a user and the CDSS 86. For example, the input interface 88 may facilitate a user interface through which the user may manually enter the at least one coefficient. Additionally, or alternatively, the input interface may provide the CDSS 86 with access to an electronic patient record from which one or more input features may be extracted. In any of these cases, the input interface is configured to collect one or more of the following input features in association with a specific patient on or before a time at which the CDSS 86 is used to assess the model's coefficients.

Time-intensity curves can be extracted from the recordings of the fluorescence images by calculating the average image intensity within each calculation region 80 for each frame in the recording. The time intensity curves can be characterized by the following parameters: Time to Max (s): The time it takes for the signal to reach its maximum intensity, starting from the beginning of the ingress phase; Ingress (i/s): Average slope of the signal curve in the ingress phase; Max Ingress (i/s): Value within the ingress phase with the maximum slope; Time to Max Ingress (s): Timestamp from the beginning of the ingress phase to time with the maximum ingress slope; Average (i): Average signal intensity; AUC (i·s) Area Under the Curve (AUC) for the signal curve; AUC10 (i·s): AUC between the start of the ingress phase and the following 10 seconds; AUC Ingress (i·s): AUC of the signal curve in the ingress phase The time intensity curve, which is for example shown in FIG. 14 can be fitted by a single-tissue compartment model, such as by the Adiabatic Approximation to the Tissue Homogeneity model (AATH), which is in principle described in Lawrence & Lee, 1998, Elliot et. al., 2020. Other fitting models can be Kang's model (Kang et. al., 2009) or the biexponential model (Gurfinkel et al. 2000, Shinohara et al. 1996).

Each model contains several coefficients that may be predictive of the clinical outcome. An additional coefficient required for all models is the arrival time of the tracer, also called the delay. This coefficient is fitted because the moment of fluorescent dye injection during acquisition is not known. The coefficients fitted in a single tissue compartment model are the following: K1 (/min); k2 (/min) (additional parameter: delay (s)). The coefficients fitted for the AATH model are the following: F (ml/min/100 g); $k_{ep}$ (/min); $t_c$ (s); E (additional parameter: delay (s)).

The goodness of fit for each of the models can be measured by calculating the adjusted R-squared ($R_{2adj}$). The $R_2$ statistic of a model (also called coefficient of determination) is a value that shows the proportion of variance in the data that is explained by the model.

The above coefficients can be applied as $1^{st}$ to $N^{th}$ input feature to the AI model.

Based on one or more of the above input features, the processor 84 performs the inference operation using the AI model to generate the output, i.e. the risk prediction value.

For example, the input interface may deliver the one or more of the relevant input features into an input layer of the AI model, which propagates these input features through the AI model to an output layer. The AI model can provide a computer system the ability to perform tasks, without explicitly being programmed, by making inferences based on patterns found in the analysis of data. AI model explores the study and construction of algorithms (e.g., machine-learning algorithms) that may learn from existing data and make predictions about new data. Such algorithms operate by building an AI model from example training data in order to make data-driven predictions or decisions expressed as outputs or assessments.

There are two common modes for machine learning (ML): supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled, and allowing the algorithm to act on that information without guidance. Unsupervised ML is useful in exploratory analysis because it can automatically identify structure in data.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In the given embodiment, the AI is trained in supervised learning.

In some examples, the AI model may be trained continuously or periodically prior to performance of the inference operation by the processor 84. Then, during the inference operation, the patient specific input features provided to the AI model may be propagated from an input layer, through one or more hidden layers, and ultimately to an output layer that corresponds to the risk prediction value.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES 2 image capturing and processing device
3 physician
4 body part 5 visible light image
6 patient
7 fluorescence image
8 fluorescent agent
9 overlay image
10 image capturing device
11 surface
12 processing device
14 display
16 illumination unit
18 objective lens
20 prism assembly
22 fluorescence imaging unit
24 visible light imaging unit
26 data link
28 stitching unit
30 superimposing unit
32 measurement unit
33 distance sensor
50 endoscope
52 optical fiber
51 fibers
54 light source
56 shaft
58 fiber bundle
60 peak frequency map unit
62 area of interest
64 output unit
66 superimposing unit
80 calculation region
82 organ
84 processor
86 CDSS
88 user interface
90 patient record
92 processing device
P1 first pentagonal prism
P2, P4 compensating prism
P3 second pentagonal prism
P5, P6, P7 dichroic prism assembly
A incoming light beam
B . . . O light beams
S1 entrance face
D1 . . . D5 sensors
C1, C2 coating
L longitudinal direction
d distance

What is claimed is:

1. A method of measuring a fluorescence signal in a tissue of a body part, to which a fluorescent agent has been added, and of imaging a surface of the body part, wherein the tissue to which the fluorescent agent has been added forms part of the body part, the method comprising:
receiving a plurality of fluorescence images, over time so as to provide a time sequence of fluorescence images, in an area of examination of the tissue illuminated with excitation light having a wavelength suitable to generate emitted light by excited emission of the fluorescent agent and by spatially resolved measurement of the emitted light so as to provide the time sequence of fluorescence images,
receiving at least one visible light image of a surface of the body part in the area of examination, wherein one or more of a viewing direction and a perspective of the fluorescence image and the visible light image are linked via a known relationship,
determining a peak frequency map for an area of interest in the plurality of fluorescence images by analyzing the time sequence of fluorescence images to:
determine a time-dependent intensity curve of at least one pixel in the area of interest,
identify peaks in the time-dependent intensity curve,
determine one or more of a frequency of the identified peaks and a maximum high of the identified peaks, and
generate a graphic representation of one or more of the determined frequency and maximum high for the at least one pixel and including the same in the peak frequency map, and
outputting the peak frequency map together with one or more of the visible light image and the fluorescence image.

2. The method of claim 1, wherein the generating of the graphic representation includes generating an intensity plot indicative of one or more of the determined frequency and the maximum high of the identified peak at a position of the least one pixel in the area of interest.

3. The method of claim 2, further comprising:
superimposing the peak frequency map and the fluorescence image so as to provide a peak/fluorescence overlay image and
one or more of outputting the peak/fluorescence overlay image as the output of the peak frequency map together with the fluorescence image and superimposing the peak frequency map and the visible light image so as to provide a peak/visible overlay image, and
outputting the peak/visible overlay image as the output of the peak frequency map together with the visible light image.

4. The method according to claim 1, wherein the receiving of the fluorescence image and the receiving of the visible light image are performed simultaneously in absence of time-switching between a signal of the fluorescence image and a signal of the visible light image.

5. The method according to claim 1, further comprising:
repeating the receiving of the fluorescence image and the receiving of the visible light image to provide a series of fluorescence images and a series of visible light images, wherein the images of the series show different overlapping areas of examination of the body part,
applying a stitching algorithm on the series of visible light images to generate a large visible light image, wherein the stitching algorithm determines and applies a set of stitching parameters,
applying the stitching algorithm on the series of fluorescence images to generate a large fluorescence image, wherein the stitching algorithm applies the set of stitching parameters determined when performing the stitching of the visible light images, and
the outputting includes outputting the large visible light image together with the large fluorescence image and the peak frequency map.

6. The method according to claim 1, wherein the measurement of the fluorescence signal is performed on a tissue, to which at least a first fluorescent agent and a second fluorescent agent have been added, wherein the receiving of the fluorescence image comprises:
receiving a first fluorescence image in a first wavelength range, which is generated by illuminating the tissue with first excitation light having a first wavelength suitable to generate emitted light by a first excited emission of the first fluorescent agent, and receiving a second fluorescence image in a second wavelength range, which is generated by illuminating the tissue with second excitation light having a second wavelength suitable to generate emitted light by a second excited emission of the second fluorescent agent, wherein the receiving of the time sequence of fluorescence images, the determining a peak frequency map and the outputting of the peak frequency map together with the visible light image are performed for each of the first fluorescence image and the second fluorescence image.

7. The method according to claim 6, wherein the receiving of the first fluorescence image and the receiving of the second fluorescence image are performed simultaneously in absence of time-switching between a signal of the first fluorescence image and a signal of the second fluorescence image.

8. An image capturing and processing device configured to measure a fluorescence signal in a tissue of a body part, to which a fluorescent agent has been added, and to image a surface of the body part, wherein the tissue to which the fluorescent agent has been added forms part of the body part, the image capturing and processing device comprising:

a processor comprising hardware, the processor being configured to:
receiving a plurality of fluorescence images over time, so as to provide a time sequence of fluorescence images, in an area of examination in which the tissue is illuminated with excitation light having a wavelength suitable to generate emitted light by excited emission of the fluorescent agent, and by spatially resolved measurement of the emitted light so as to provide the fluorescence image,
receive a visible light image of a surface of the body part in the area of examination, wherein one or more of a viewing direction and a perspective of the fluorescence image and the visible light image are linked via a known relationship,
determine a peak frequency map for an area of interest in the fluorescence images by analyzing the time sequence of fluorescence images,
determine a time-dependent intensity curve of at least one pixel in the area of interest,
identify peaks in the time-dependent intensity curve;
determine a frequency of the identified peaks and a maximum high of the identified peaks,
generate one or more of a graphic representation of the determined frequency and maximum high for the at least one pixel and including the same in the peak frequency map, and
output the peak frequency map together with one or more of the visible light image and the fluorescence image.

9. The device of claim 8, wherein the generation of the graphic representation includes generating an intensity plot, which is indicative of one or more of the determined frequency and the maximum high of the identified peak at a position of the least one pixel in the area of interest.

10. The device of claim 9, wherein the processor is further configured to:
superimpose the peak frequency map and the fluorescence image so as to provide a peak/fluorescence overlay image,
one or more of output the peak/fluorescence overlay image as the output of the peak frequency map together with the fluorescence image and superimpose the peak frequency map and the visible light image so as to provide a peak/visible overlay image, and
output the peak/visible overlay image as the output of the peak frequency map together with the visible light image.

11. The device according to claim 8, wherein the receiving of the visible light image comprises receiving a series of visible light images, wherein each of the series of fluorescence images and the series of visible light images show different overlapping areas of examination of the body part, wherein the processor is further configured to:
apply a stitching algorithm on the series of visible light images and to generate a large visible light image, wherein the stitching algorithm determines and applies a set of stitching parameters, and
apply the stitching algorithm on the series of fluorescence images and to generate a large fluorescence image, wherein the stitching algorithm applies the set of stitching parameters determined when performing the stitching of the visible light images, and
output the large visible light image together with the large fluorescence image and the peak frequency map.

12. The device according to claim 8, wherein
the receiving of the visible light image comprises receiving a series of visible light images, wherein the series of fluorescence images and the series of visible light images each show different overlapping areas of examination of the body part, the processor being further configured to:
apply a stitching algorithm on the series of visible light images to generate a large visible light image, wherein the stitching algorithm determines and applies a set of stitching parameters,
apply the stitching algorithm on the series of fluorescence images to generate a large fluorescence image, wherein the stitching algorithm applies the set of stitching parameters determined when performing the stitching of the visible light images, and
output the large visible light image together with the large fluorescence image and the peak frequency map.

13. The device according to claim 8, wherein in the received series of fluorescent images and the visible light image, the viewing direction and the perspective are identical.

14. The device according to claim 13, wherein the received series of fluorescent images and the visible light image are captured through a same objective lens.

15. The device according to claim 8, wherein the series of fluorescence images and the visible light image are captured simultaneously in absence of time-switching between a signal of the fluorescence image and a signal of the visible light image.

16. The device according to claim 8, further comprising an image capturing device having a fluorescent image sensor and a visible image sensor, the image capturing device comprising: a dichroic prism assembly configured to receive fluorescent light forming the series of fluorescence images and visible light forming the visible light image through an entrance face, the dichroic prism assembly comprising:
a first prism, a second prism, a first compensator prism located between the first prism and the second prism,
a second dichroic prism assembly for splitting the visible light in three light components, and
a second compensator prism located between the second prism and the second dichroic prism assembly, wherein the first prism and the second prism each have a cross section with at least five corners, each corner having an inside angle of at least 90 degrees, wherein the corners of the first prism and the second prism each have a respective entrance face and a respective exit face, and are each configured so that an incoming beam which enters the entrance face of the respective first and second prisms in a direction parallel to a normal of said entrance face is reflected twice inside the respective first and second prisms and exits the respective first prism and second prisms through their exit face parallel to a normal of said exit face, wherein the normal of the entrance face and the normal of the exit face of the respective first prism and second prism are perpendicular to each other;

wherein, when light enters the first prism through the entrance face, the light is partially reflected towards the exit face of the first prism thereby traveling a first path length from the entrance face of the first prism to the exit face of the first prism, and the light partially enters the second prism via the first compensator prism and is partially reflected towards the exit face of the second prism, thereby traveling a second path length from the entrance face of the first prism to the exit face of the second prism, and wherein the first prism is larger than the second prism so that the first and the second path lengths are the same.

17. A method of diagnosing lymphatic dysfunction comprising:

receiving measurement of a fluorescence signal in a tissue of the body part, to which a fluorescent agent has been administered, and of receiving a plurality of fluorescent images and a visible light image of a surface of the body part, wherein the tissue to which the fluorescent agent has been added forms part of the body part, receiving the plurality of fluorescence images over time, so as to provide a time sequence of fluorescence images, of the tissue illuminated with excitation light having a wavelength suitable to generate emitted light by excited emission of the fluorescent agent, and by spatially resolved measurement of the emitted light so as to provide the fluorescence image, receiving the visible light image of the surface of the body part in the area of examination, wherein one or more of a viewing direction and a perspective of the fluorescence image and the visible light image are linked via a known relationship, determining a peak frequency map for an area of interest in the fluorescence images by analyzing the time sequence of fluorescence images, the analyzing comprising:

determining a time-dependent intensity curve of at least one pixel in the area of interest, identifying peaks in the time-dependent intensity curve, determining one or more of a frequency of the identified peaks and a maximum high of the identified peaks, and generating one or more of a graphic representation of the determined frequency and maximum high for the at least one pixel and including the same in the peak frequency map, outputting the peak frequency map together with one or more of the visible light image and the fluorescence image, and deriving a diagnostic result relative to the lymphatic dysfunction by analyzing the fluorescence image and the peak frequency map.

18. The method according to claim 17, wherein the receiving of the plurality of fluorescence images and the receiving of the visible light image are performed simultaneously in absence of time-switching between a signal of the fluorescence image and a signal of the visible light image.

19. The method according to claim 17, wherein the fluorescent agent is administered to an arm or leg of a patient by injecting the fluorescent agent in tissue between phalanges of the foot or hand of the patient.

20. A method of long-term therapy of lymphatic dysfunction comprising:

performing a diagnosis relative to lymphedema by performing the method of claim 17 on a patient, performing a therapy on the patient, the therapy being adjusted to the diagnostic result relative to the lymphatic dysfunction, and repeating the diagnosing of the lymphatic dysfunction, and performing a therapy on the patient, wherein in each iteration of the repeating, the therapy is adjusted to the diagnosis of the lymphatic dysfunction.

21. A method of providing a risk prediction value based on measuring of a fluorescence signal in a tissue of a body part, to which a fluorescent agent has been added, wherein the tissue to which the fluorescent agent has been added forms part of the body part, the method comprising:

receiving a plurality of fluorescence images, over time so as to provide a time sequence of fluorescence images, in an area of examination in which the tissue is illuminated with excitation light having a wavelength suitable to generate emitted light by excited emission of the fluorescent agent and by spatially resolved measurement of the emitted light so as to provide the fluorescence image, defining at least one calculation region in the at least one fluorescence image of the sequence of fluorescence images, calculating a time-intensity curve from a signal intensity in the calculation region, approximating the time-intensity curve by a model having at least one coefficient and determining the at least one coefficient that is related to an approximation of the model to at least a portion of the time-intensity curve;

providing the at least one coefficient to an input interface of a processor, wherein the processor comprises the input interface, an artificial intelligence (AI) model and an output interface, and wherein the processor performs an inference operation by applying the at least one coefficient to the AI model and by generating a risk prediction value, which is indicative of a tissue perfusion in the calculation region, as output data at the output interface, from an output of the AI model, and communicating the risk prediction value via a user interface.

22. The method according to claim 21, wherein:

the defining of the calculation region, the calculating of the time-intensity curve, the approximating of the time-intensity curve by the model and determining the at least one coefficient, the providing of the at least one coefficient to an input interface of the processor, and the performing of the inference operation and the generating and outputting of the risk prediction value based on the AI model, are each performed for a plurality of calculation regions for every pixel or voxel of the fluorescence image, the method further comprising:

converting the risk prediction values across the plurality of calculation regions into a risk prediction value-derived image map, and
outputting the risk prediction value-derived image map via the user interface.

23. The method according to claim 22, wherein
the defining of the calculation region,
the calculating of the time-intensity curve,
the approximating of the time-intensity curve by the model and determining the at least one coefficient,
the providing of the at least one coefficient to an input interface of the processor, and
the performing of the inference operation and the generating and outputting of the risk prediction value based on the AI model,
are each performed for the plurality of calculation regions for every pixel or voxel of the fluorescence image.

24. The method according to claim 21, further comprising:
receiving at least one visible light image of a surface of the body part in the area of examination, wherein one or more of a viewing direction and a perspective of the plurality of fluorescence images and the visible light image are linked via a known relationship, and
outputting the risk prediction value and the visible light image via the user interface.

25. The method according to claim 22, further comprising:
receiving at least one visible light image of a surface of the body part in the area of examination, wherein one or more of a viewing direction and a perspective of the fluorescence image and the visible light image are linked via a known relationship, and
outputting the risk prediction value-derived image map as overlay image together with the visible light image via the user interface.

26. The method according to claim 21, wherein the model applied for approximating the time-intensity curve is a single-tissue compartment model.

27. The method according to claim 26, wherein the single-tissue compartment model is an Adiabatic Approximation to the Tissue Homogeneity (AATH) model.

28. The method according to claim 21, wherein the artificial intelligence model is a pre-trained neural network.

29. The method according to claim 28, wherein the pre-trained neural network is trained in supervised training on the basis of clinical patient data.

30. A computer-based clinical decision support system (CDSS) for providing of a risk prediction value based on a measurement of a fluorescence signal in a tissue of a body part, to which a fluorescent agent has been added, wherein the tissue to which the fluorescent agent has been added forms part of the body part, the CDSS comprising:
one or more processors comprising hardware, the one or more processors being configured to:
receive a series of fluorescence images, over time so as to provide a time sequence of fluorescence images, in an area of examination in which the tissue is illuminated with excitation light having a wavelength suitable to generate emitted light by excited emission of the fluorescent agent and by spatially resolved measurement of the emitted light so as to provide the fluorescence image,
define at least one calculation region in the at least one fluorescence image of the sequence of fluorescence images,
calculate a time-intensity curve from a signal intensity in the calculation region,
approximate the time-intensity curve by a model having at least one coefficient and to determine the at least one coefficient that is related to an approximation of the model to at least a portion of the time-intensity curve;
provide the at least one coefficient to an input interface, an artificial intelligence model and an output interface,
perform an inference operation by applying the at least one coefficient to the AI model and by generating a risk prediction value, which is indicative of a tissue perfusion in the calculation region, as output data at the output interface, from an output of the AI model, and to communicate the risk prediction value to a user interface, and
display the risk prediction value.

31. The CDSS according to claim 30, wherein the one or more processors being configured to:
define the calculation region,
calculate the time-intensity curve,
approximate the time-intensity curve by the model and to determine the at least one coefficient,
provide the at least one coefficient to the input interface,
perform the inference operation and to generate and output the risk prediction value based on the AI model,
for a plurality of calculation regions,
wherein the one or more processors being further configured to:
convert the risk prediction values across the plurality of calculation regions into a risk prediction value-derived image map,
communicate the risk prediction value-derived image map to the user interface, and
display the risk prediction value-derived image map.

32. The CDSS according to claim 31, wherein the one more processors being configured to:
define the calculation region,
calculate the time-intensity curve,
approximate the time-intensity curve by the model and to determine the at least one coefficient,
provide the at least one coefficient to the input interface,
perform the inference operation and to generate and output the risk prediction value based on the AI model,
for a plurality of calculation regions, for every pixel or voxel of the fluorescence image.

33. The CDSS according to claim 30, wherein the one or more processors being further configured to:
receive at least one visible light image of a surface of the body part in the area of examination, wherein one or more of a viewing direction and a perspective of the fluorescence image and the visible light image are linked via a known relationship,
output the risk prediction value and the visible light image to the user interface, and
display the risk prediction value and the visible light image.

34. The CDSS according to claim 30, wherein the one or more processors being further configured to:
receive at least one visible light image of a surface of the body part in the area of examination, wherein one or more of a viewing direction and a perspective of the fluorescence image and the visible light image are linked via a known relationship, and
output the risk prediction value-derived image map and the visible light image to the user interface, and display the risk prediction value-derived image map as overlay image together with the visible light image.

35. The CDSS according to claim 30, wherein the one or more processors comprise the model applied for approximating the time-intensity curve, which is a single-tissue compartment model.

36. The CDSS according to claim 35, wherein the single-tissue compartment model is an Adiabatic Approximation to the Tissue Homogeneity (AATH) model.

37. The CDSS according to claim 30, wherein the one or more processors comprise the artificial intelligence (AI) model, which is a pre-trained neural network.

38. The CDSS according to claim 37, wherein the pre-trained neural network is a pre-trained neural network that was trained in supervised training on the basis of clinical patient data.

* * * * *